(12) United States Patent
Koike et al.

(10) Patent No.: US 9,561,156 B2
(45) Date of Patent: Feb. 7, 2017

(54) COINFUSION APPARATUS

(71) Applicant: YUYAMA MFG. CO., LTD., Toyonaka-shi, Osaka (JP)

(72) Inventors: Naoki Koike, Toyonaka (JP); Akifumi Tanaka, Toyonaka (JP)

(73) Assignee: YUYAMA MFG. CO., LTD., Toyonaka-shi (JP)

( * ) Notice: Subject to any disclaimer, the term of this patent is extended or adjusted under 35 U.S.C. 154(b) by 149 days.

(21) Appl. No.: 14/480,568

(22) Filed: Sep. 8, 2014

(65) Prior Publication Data

US 2014/0373975 A1    Dec. 25, 2014

Related U.S. Application Data

(63) Continuation of application No. 14/114,803, filed as application No. PCT/JP2012/070048 on Aug. 7, 2012, now Pat. No. 8,857,476.

(30) Foreign Application Priority Data

Aug. 8, 2011   (JP) ................................. 2011-172692

(51) Int. Cl.
*A61J 1/20*   (2006.01)
*A61J 3/00*   (2006.01)
(Continued)

(52) U.S. Cl.
CPC ................. *A61J 1/2096* (2013.01); *A61J 1/22* (2013.01); *A61J 3/002* (2013.01); *B25J 11/009* (2013.01);
(Continued)

(58) Field of Classification Search
CPC .............. A61J 1/2096; A61J 1/22; A61J 1/10; A61J 3/002; A61J 2200/74; B25J 11/009; A61M 5/14; A61M 2209/045
(Continued)

(56) References Cited

U.S. PATENT DOCUMENTS 5,341,854 A * 8/1994 Zezulka .................... A61J 1/20
                                                                141/1
5,431,201 A * 7/1995 Torchia ..................... A61J 1/20
                                                              141/100
(Continued)

FOREIGN PATENT DOCUMENTS

CN     101511461 A     8/2009
EP     1779830 A1      5/2007
(Continued)

OTHER PUBLICATIONS

European Search Report, issued on Nov. 6, 2014 from European Patent Office by EPO, Application No. 12822347.6.
(Continued)

*Primary Examiner* — Nicholas A Arnett
(74) *Attorney, Agent, or Firm* — Masuvalley & Partners

(57) ABSTRACT

A coinfusion apparatus including a coinfusion operation section; a coinfusion processing room; a supply section; and a transfusion bag retention section. The coinfusion operation section consists of first and second robot arms. The first robot arm retains a medical agent container. The second robot arm performs an operation to insert a syringe needle of a syringe to a mouth section of the medical agent container and an operation to insert the syringe needle of the syringe to a coinfusion mouth of the transfusion bag. The coinfusion processing room holds the coinfusion operation section. The supply section supplies the medical agent container and the syringe into the coinfusion processing room. The transfusion bag retention section retains the transfusion bag at the outer side of the coinfusion processing room and positions the coinfusion mouth of the transfusion bag at the coinfusion communication mouth formed in the coinfusion processing room.

17 Claims, 18 Drawing Sheets

(51) Int. Cl.
*A61J 1/22* (2006.01)
*B25J 11/00* (2006.01)
*A61J 1/10* (2006.01)
*A61M 5/14* (2006.01)

(52) U.S. Cl.
CPC ............... *A61J 1/10* (2013.01); *A61J 2200/74* (2013.01); *A61M 5/14* (2013.01); *A61M 2209/045* (2013.01)

(58) Field of Classification Search
USPC ...... 141/18, 25, 27, 114, 313–315, 370, 372
See application file for complete search history.

(56) References Cited

U.S. PATENT DOCUMENTS

| | | | | | |
|---|---|---|---|---|---|
| 7,610,115 | B2* | 10/2009 | Rob | ............ | A61J 1/20 318/568.11 |
| 7,783,383 | B2* | 8/2010 | Eliuk | ............ | A61J 1/20 141/1 |
| 7,930,066 | B2* | 4/2011 | Eliuk | ............ | A61J 1/20 221/191 |
| 8,151,835 | B2* | 4/2012 | Khan | ............ | B65B 3/003 141/10 |
| 8,386,070 | B2* | 2/2013 | Eliuk | ............ | A61J 1/20 141/1 |
| 8,499,919 | B2* | 8/2013 | Giribona | ............ | B65B 3/003 198/346.1 |
| 8,539,989 | B2* | 9/2013 | Giribona | ............ | B65B 3/003 141/2 |
| 8,571,708 | B2* | 10/2013 | Rob | ............ | A61J 1/20 318/568.11 |
| 8,632,738 | B2* | 1/2014 | Giribona | ............ | B65B 3/003 422/500 |
| 8,857,476 | B2* | 10/2014 | Koike | ............ | A61J 3/002 141/114 |
| 9,043,019 | B2* | 5/2015 | Eliuk | ............ | A61J 1/20 221/191 |
| 9,173,816 | B2* | 11/2015 | Reinhardt | ............ | A61J 1/00 |
| 2006/0136095 | A1* | 6/2006 | Rob | ............ | A61J 1/20 700/245 |
| 2006/0259195 | A1* | 11/2006 | Eliuk | ............ | A61J 1/20 700/245 |
| 2008/0051937 | A1* | 2/2008 | Khan | ............ | B65B 3/003 700/240 |
| 2009/0067973 | A1 | 3/2009 | Eliuk et al. | | |
| 2010/0006602 | A1 | 1/2010 | Giribona et al. | | |
| 2010/0198392 | A1 | 8/2010 | Eliuk et al. | | |
| 2011/0172810 | A1* | 7/2011 | Mlodzinski | ............ | A61J 1/20 700/230 |
| 2011/0208350 | A1* | 8/2011 | Eliuk | ............ | A61J 1/20 700/240 |
| 2012/0048418 | A1* | 3/2012 | Giribona | ............ | B65B 3/003 141/1 |
| 2012/0048419 | A1* | 3/2012 | Giribona | ............ | B65B 3/003 141/1 |
| 2012/0048424 | A1* | 3/2012 | Giribona | ............ | B65B 3/003 141/311 R |
| 2012/0048675 | A1* | 3/2012 | Giribona | ............ | B65B 3/003 198/346.2 |
| 2012/0048676 | A1* | 3/2012 | Giribona | ............ | B65B 3/003 198/346.2 |
| 2012/0051971 | A1* | 3/2012 | Giribona | ............ | B65B 3/003 422/63 |
| 2014/0031976 | A1* | 1/2014 | Reinhardt | ............ | A61J 1/00 700/239 |
| 2014/0174600 | A1* | 6/2014 | Koike | ............ | A61J 3/002 141/89 |
| 2015/0210410 | A1* | 7/2015 | Umeno | ............ | A61J 1/2096 53/51 |

FOREIGN PATENT DOCUMENTS

| | | |
|---|---|---|
| EP | 2298270 A1 | 3/2011 |
| JP | 01-244759 A | 9/1989 |
| JP | 07-051385 A | 2/1995 |
| JP | 2000-356642 A | 12/2000 |
| JP | 2002-092165 A | 3/2002 |
| JP | 2006-311869 A | 11/2006 |
| JP | 2009-504199 A | 2/2009 |
| JP | 2009-544391 A | 12/2009 |
| JP | 2010-509002 A | 3/2010 |

OTHER PUBLICATIONS

Japan Patent Office, Notification of Reasons for Refusal issued on Jul. 7, 2015, Application No. JP2012-251019, total 6 pages with translation.
SIPO, Second Office Action issued in Chinese Patent Application No. 2012800385319, issued on Sep. 9, 2016, total 6 pages with English translation.

* cited by examiner

COINFUSION APPARATUS

This application claims priority under 35 U.S.C. §120 as a continuation of U.S. patent application Ser. No. 14/114, 803, filed Oct. 30, 2013, which is a national phase application under 35 U.S.C. §371 of International Application No. PCT/JP2012/070048, filed on Aug. 7, 2012, and claims priority under 35 U.S.C. §119 to Japanese Patent Application No. 2011-172692, filed on Aug. 8, 2011, which are hereby expressly incorporated by reference in their entirety for all purposes.

TECHNICAL FIELD

This invention relates to a coinfusion apparatus for mixing and adjusting medical agent such as anticancer drug with transfusion (replacement fluid).

BACKGROUND ART

Medical agent such as anticancer drug mixed in transfusion causes a risk of radiation exposure. Therefore, a coinfusion processing in which such a medical agent or the like is mixed and adjusted with transfusion is performed in a safety cabinet set to have a negative pressure. Then, when coinfusion is carried out by a vial container filled with powder medical agent as the above-mentioned medical agent, a medical agent preparator sucks the transfusion from a transfusion bag by a syringe and inserts the syringe needle of this syringe to a cap section (rubber plug) of the vial container to inject the transfusion in the syringe into the vial container. Then, the medical agent preparator uses the syringe to suck the transfusion in which the medical agent has been dissolved. Since the medical agent in a fixed amount is filled in the vial container, the medical agent preparator repeatedly performs an operation of injecting the transfusion into a plurality of vial containers and sucking it until the required amount of the medical agent is dissolved in the transfusion. After the required amount of the medical agent is dissolved in the transfusion, the medical agent preparator inserts the syringe needle to the coinfusion mouth of the transfusion bag to return, into the transfusion bag, the transfusion containing the medical agent dissolved therein in the syringe.

The coinfusion processing is not limited to the vial container, and the coinfusion processing in which the medicinal solution in an ampule is injected into the transfusion is also performed. In such a coinfusion processing using an ampule, medicinal solution in an ampule with its head cut off is sucked into a syringe and the syringe needle is inserted to the coinfusion mouth of a transfusion bag, thereby injecting the medicinal solution in the syringe into the transfusion bag.

Here, Japanese Laid-Open Publication No. H1-244759 (Hereinafter Patent Document 1) discloses a radioactive medical agent dispensing apparatus for performing a dispensing operation while avoiding radiation exposure due to radioactive medical agent. However, in Patent Document 1, the apparatus is not designed to be used as a coinfusion apparatus for injecting medicinal solution into a transfusion bag, and there is no disclosure regarding a technique for preventing the transfusion bag from being exposed to radiation.

In view of the above-mentioned situation, embodiments of the present invention provides a coinfusion apparatus that can automatically perform a part or the entirety of the coinfusion processing and that can prevent the transfusion bag from being subjected to radiation exposure.

SUMMARY OF THE INVENTION

Embodiments of the present invention provides a coinfusion apparatus including: a coinfusion operation section comprising a container retention section for retaining a medical agent container and a syringe retention section for retaining a syringe and for changing an insertion amount of a piston part to a cylinder part in the syringe, the coinfusion operation section being configured to perform an operation to insert a syringe needle of the syringe to a mouth section of the medical agent container retained by the container retention section and an operation to insert the syringe needle of the syringe to a coinfusion mouth of a transfusion bag; a coinfusion processing room accommodating the coinfusion operation section; and a transfusion bag retention section for retaining the transfusion bag at an outer side of the coinfusion processing room and for positioning the coinfusion mouth of the transfusion bag at a coinfusion communication mouth formed at the coinfusion processing room.

By the configuration described above, a part or the entirety of the coinfusion processing can be performed automatically by a coinfusion operation section including the container retention section, a syringe retention section, and an insertion operation section. Also, the transfusion bag is provided in the outside of the coinfusion processing room, and therefore, it is possible to prevent the transfusion bag from being exposed to radiation.

The coinfusion apparatus may have a supply section for supplying the medical agent container and the syringe into the coinfusion processing room, wherein the coinfusion communication mouth and the transfusion bag retention section may be provided at same side as a side where the supply section is provided.

The transfusion bag retention section may be accommodated in a preparation container in which the medical agent container, the syringe, and the coinfusion bag are set, and the medical agent container and the syringe may be configured to be supplied from the preparation container into the coinfusion processing room. This consequently eliminates the need to remove the transfusion bag from the adjustment container. Thus, there is no need to rewrite patient information or prescription information displayed on the preparation container or patient information or prescription information recorded on an IC tag attached to the preparation container (e.g., Radio Frequency Identification (RFID)).

The coinfusion apparatus may further comprise a supply section for supplying the medical agent container and the syringe into the coinfusion processing room, wherein the coinfusion communication mouth and the transfusion bag retention section may be provided at opposite side to a side where the supply section is provided. This configuration may also be configured such that the transfusion bag is taken out from a preparation container in which the medical agent container, the syringe, and the coinfusion bag are set, and the transfusion bag is delivered to the transfusion bag retention section.

The coinfusion apparatus may also include a bagging apparatus for bagging the transfusion bag having been subjected to a coinfusion processing. It may be held either in a preparation container in which the medical agent container, the syringe, and the transfusion bag are set or in another container different from the adjustment container.

The coinfusion apparatus may also include a cleaning tool for cleaning the coinfusion mouth of the transfusion bag.

Alternatively, the coinfusion apparatus having the preparation container in which a medical agent container, a syringe, and a transfusion bag are set includes therein the transfusion bag retention section may also be configured so that the container retention section and the syringe retention section are provided separately at a left or right side in the coinfusion processing room, and a transfer section for transferring the preparation container from a position close to the container retention section to a position close to the syringe retention section is provided, and when the preparation container is transferred to the position close to the container retention section, an operation is performed to supply the medical agent container and the syringe into the coinfusion processing room, and when the preparation container is transferred to the position close to the syringe retention section, an operation is performed to position the coinfusion mouth of the transfusion bag retained by the transfusion bag retention section in the preparation container at the coinfusion communication mouth formed in the coinfusion processing room.

A dust box may be provided at lower side of the coinfusion processing room so as to communicate with the coinfusion processing room, wherein the transfer section transfers the preparation container through lower side of the coinfusion processing room and rear side of the dust box. This consequently allows the dust box to be inserted to and from the front side of coinfusion apparatus.

The preparation container may include therein a medicine tray on which the medical agent container and the syringe are placed and the transfusion bag retention section, and the medicine tray is exposed to the coinfusion processing room when a shutter providing communication between the transfer section and the coinfusion processing room is opened. It is preferable that the transfer section have a higher pressure than in the coinfusion processing room.

The coinfusion apparatus may include a robot arm functioning as the container retention section, and the robot arm may grip a syringe placed in the coinfusion processing room to make the syringe received by the syringe retention section.

The coinfusion apparatus of this invention for moving medicinal solution in a medical agent container into a transfusion bag is characterized by comprising: a robot arm for retaining the medical agent container; and a robot arm for retaining a syringe and for changing an insertion amount of a piston part to a cylinder part in the syringe, wherein the robot arm performs an operation to insert a syringe needle of the syringe to a mouth section of the medical agent container and an operation to insert the syringe needle of the syringe to a coinfusion mouth of a transfusion bag. The coinfusion apparatus may also be configured such that the syringe needle is pulled out from the coinfusion mouth of the transfusion bag while the coinfusion mouth being directed in an upward direction.

According to the invention, a part or the entirety of the coinfusion processing can be performed automatically. Furthermore, the transfusion bag is placed in the outside of the coinfusion processing room, and therefore, it is possible to prevent the transfusion bag from being exposed to radiation.

BRIEF DESCRIPTION OF DRAWING

The present disclosure is described in conjunction with the appended figures.

DETAILED DESCRIPTION OF EMBODIMENTS

Figure 1:
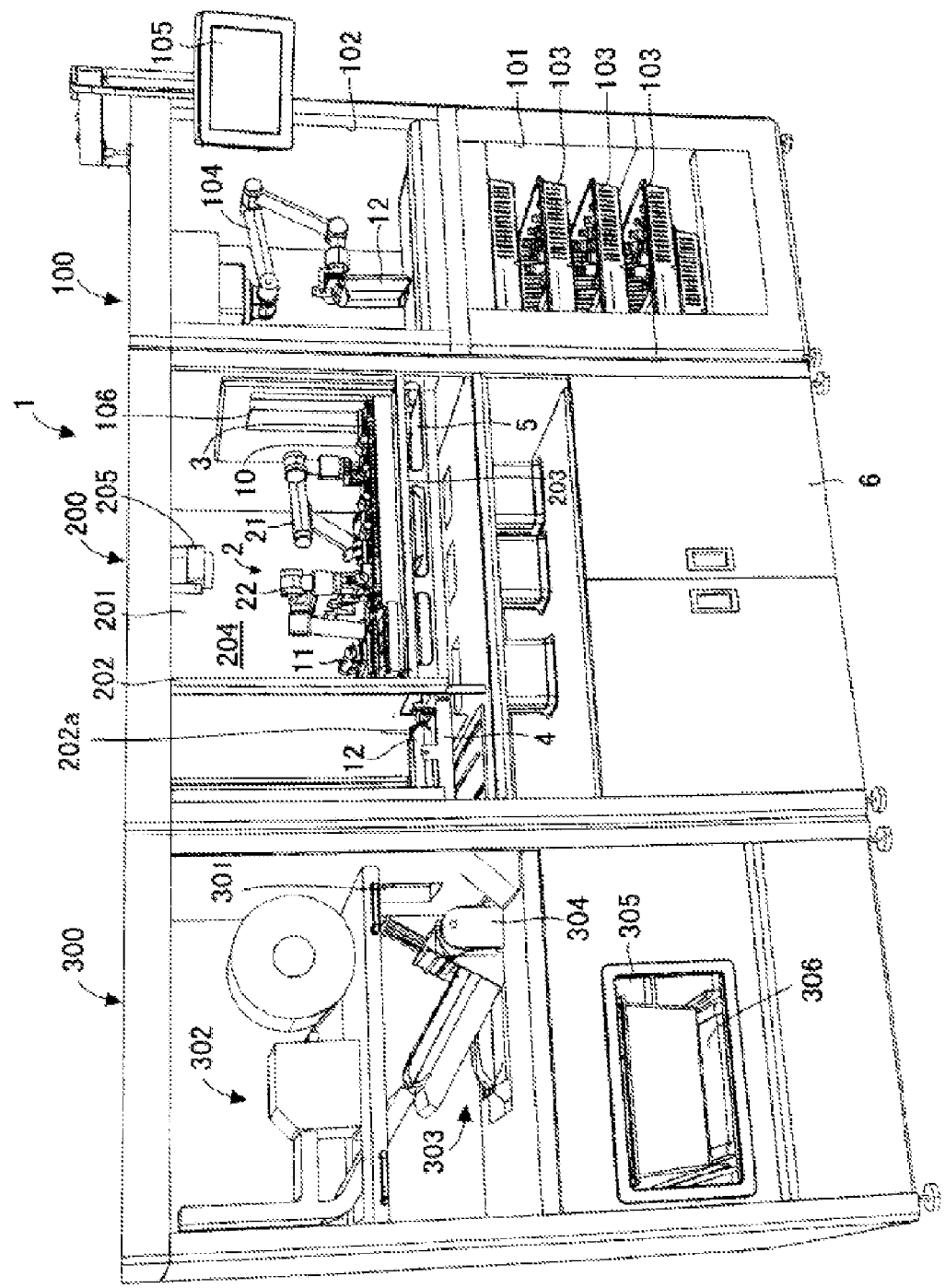
FIG. 1 is a perspective view illustrating a coinfusion apparatus according to one embodiment of this invention.

The following section will describe embodiments of the present invention with reference to the attached drawings. As shown in FIG. 1, a coinfusion apparatus 1 consists of a supply section 100, a main body section 200, and a bagging apparatus 300.

The supply section 100 consists of the container storage room 101 and a supply control room 102 formed on this the container storage room 101. The container storage room 101 can store a plurality of adjustment containers 103. The adjustment containers 103 are designed to be circulated in a gondola lift-like manner, for example, and the uppermost preparation container 103 is positioned in the supply control room 102. Each of the adjustment containers 103 contains a syringe 11, a medical agent container 10, a transfusion bag 12 and the like for each patient or each application, and such adjustment containers 103 are stored in a container storage room 101.

For example, each of the adjustment containers 103 has a text recognized by a person such as a patient name as well as a bar code for allowing the controller (microcomputer) of the coinfusion apparatus 1 to recognize various pieces of information. For example, when the preparation container 103 is positioned in the supply control room 102, the bar code attached to the preparation container 103 is read by a bar code reader, which is not shown. Then, the controller recognizes the details of a coinfusion processing to be started. Specifically, the controller reads information identified by the above read barcode including patient information, doctor information, coinfusion operation program, detailed prescription information (e.g., the type and the number of the medical agent to be used), adjustment procedure information (a drug to be dissolved with/a drug to be dissolved to, operation details, capacity/dissolved amount, removed amount) from a storage section (not shown). The coinfusion operation program may be different depending on the type of the medical agent container 10 (e.g., whether a vial container including powder-like medical agent or an ampule is used). The number of the repetition of a predetermined operation is determined based on the number of the medical agent containers 10 to be used.

Then, the controller allows the display 105 to display the detailed-prescription information and the adjustment procedure information. The adjustment procedure information is displayed in a table in which the horizontal axis shows the drug to be dissolved with/the drug to be dissolved to and the operation details while the vertical axis shows time (steps). For example, the column for the first step for "the drug to be dissolved with/the drug to be dissolved to" includes the description of "transfusion C 500 ml", and the operation column includes the description of "removal". The display 105 may also display other pieces of information.

In the supply control room 102, a supply robot 104 with its base end section fixed to the ceiling side is provided. The supply robot 104 is controlled by the controller, and the supply robot 104 performs an operation to remove the medical agent container 10, the syringe 11, the transfusion bag 12 and the like set in the preparation container 103. When the supply control room 102 has one preparation container 103 positioned thereto, and when the layout of the medical agent container 10, the syringe 11, the transfusion bag 12 and the like in the preparation container 103 is predetermined, the medical agent container 10, the syringe 11, and the transfusion bag 12 can be accurately removed by the supply robot 104 without the need to image the preparation container 103 to subject the resultant image to an image recognition, for example. Another configuration may be used in which, when the transfusion bag 12 or the like is taken out by the supply robot 104, a bar code attached to the transfusion bag 12 or the like is read by a bar code reader (not shown) so that the controller can judge whether the transfusion bag specified by the detailed-prescription information is used or not.

Figure 2:
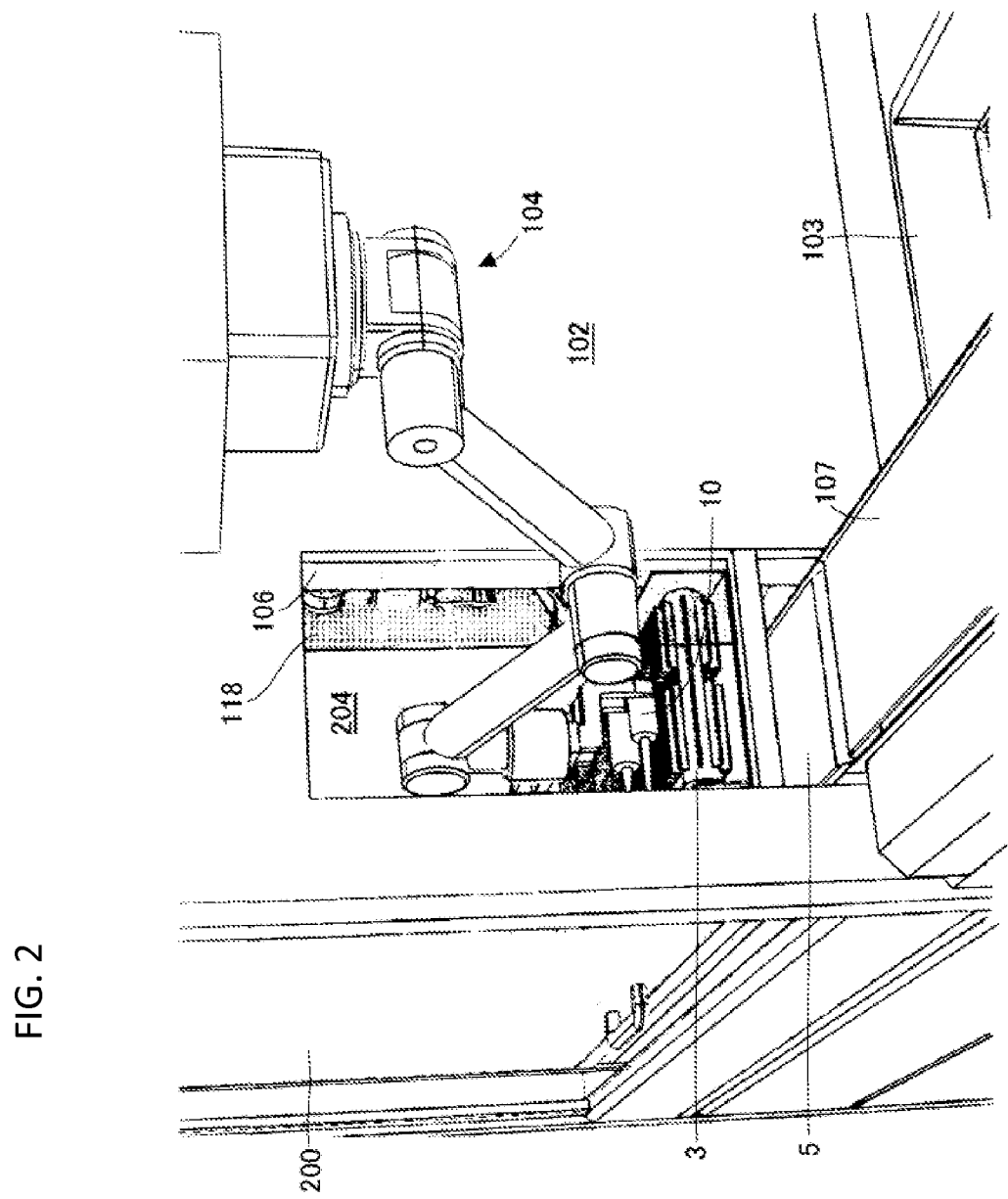
FIG. 2 is a perspective view illustrating the supply section of the coinfusion apparatus of FIG. 1.

Also as shown in FIG. 2, the communication mouth 106 allows the supply control room 102 to connect with the coinfusion processing room 204 of the main body section 200. The supply robot 104 transfers the medical agent container or the like removed from the preparation container 103 through the communication mouth 106 onto the crimped belt conveyor section 3 provided in the coinfusion processing room 204. The communication mouth 106 includes the shutter 118 that is opened by the controller when transferring the medical agent container or the like to the crimped belt conveyor section 3.

Figure 3:
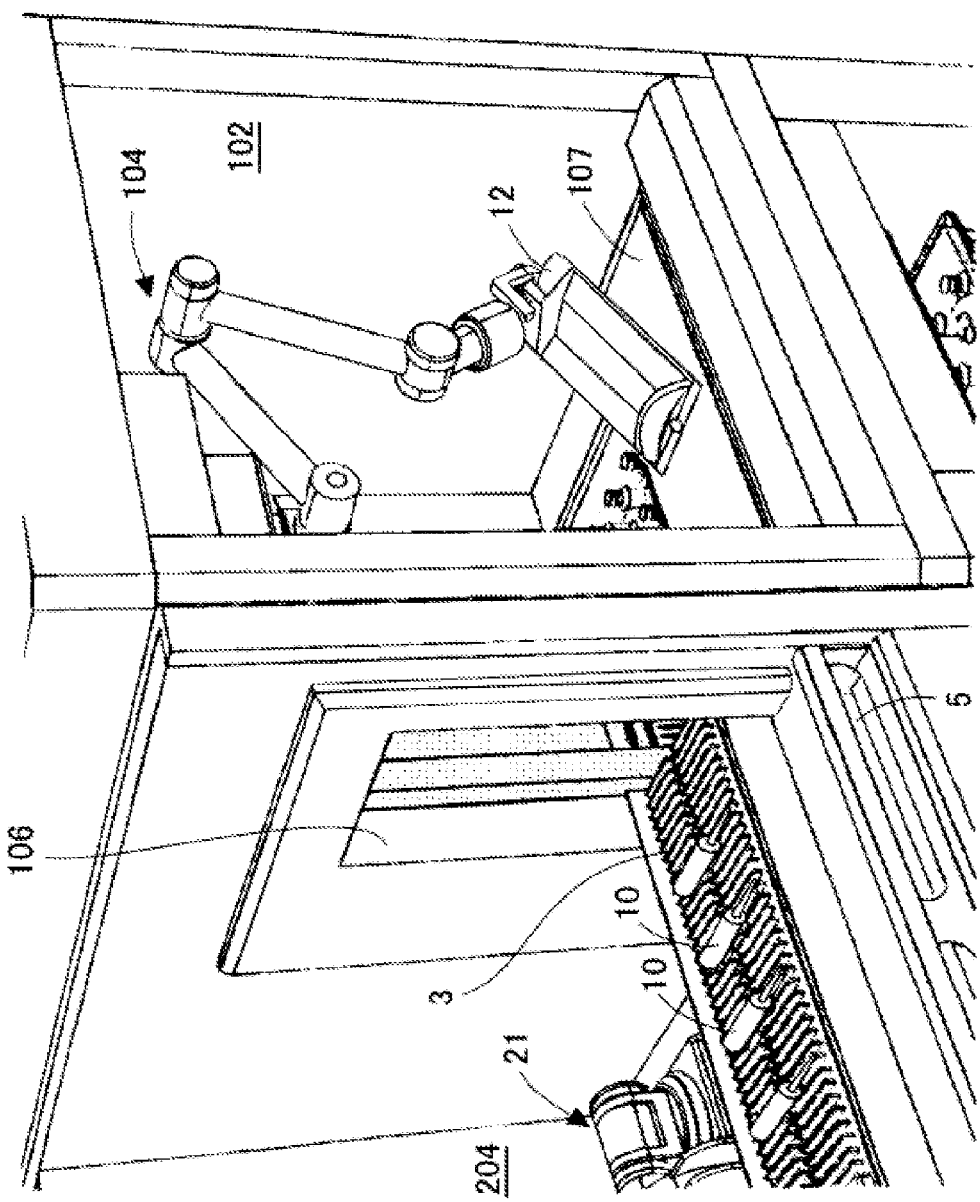
FIG. 3 is a perspective view illustrating the supply section and the main body section of the coinfusion apparatus of FIG. 1.

Also, as shown in FIG. 3, the supply robot 104 places the transfusion bag 12 taken out from the preparation container 103 onto the conveyor 107. This conveyor 107 is provided at the communication mouth 106 in the vicinity of the transfusion bag conveying section 5 that is made of a conveyor as well. The transfusion bag 12 placed on the conveyor 107 is transferred to the transfusion bag conveying section 5. The transfusion bag conveying section 5 is provided at the outer side (the lower side in this example) of the coinfusion processing room 204. Thus, the transfusion bag 12 is transferred without passing through the coinfusion processing room 204.

As shown in the above-mentioned FIG. 1, the main body section 200 includes: the coinfusion operation section 2; the crimped belt conveyor section 3; the transfusion bag retention section 4; the transfusion bag conveying section 5; and the dust section 6. In this embodiment, the safety cabinet 201, which is set to have a negative pressure, includes the coinfusion operation section 2, the crimped belt conveyor section 3, the transfusion bag retention section 4, and the transfusion bag conveying section 5. A division plate 202 and a division floor 203 constitute the coinfusion processing room 204. This coinfusion processing room 204 includes therein the coinfusion operation section 2 and the crimped belt conveyor section 3. The outside of the coinfusion processing room 204 has the transfusion bag retention section 4 and the transfusion bag conveying section 5. Another configuration may also be used in which the outer side of the safety cabinet 201 (an atmospheric pressure space) includes therein the transfusion bag retention section 4 and the transfusion bag conveying section 5. In this configuration, the safety cabinet 201 itself functions as a coinfusion processing room.

The coinfusion operation section 2 consists of the first robot arm 21 provided on the supply section 100-side and the second robot arm 22 provided on the transfusion bag retention section 4-side, and carries out an insertion operation, which will be described later. The first robot arm 21 and the second robot arm 22 have the base end sections fixed to the floor side.

Figure 4:
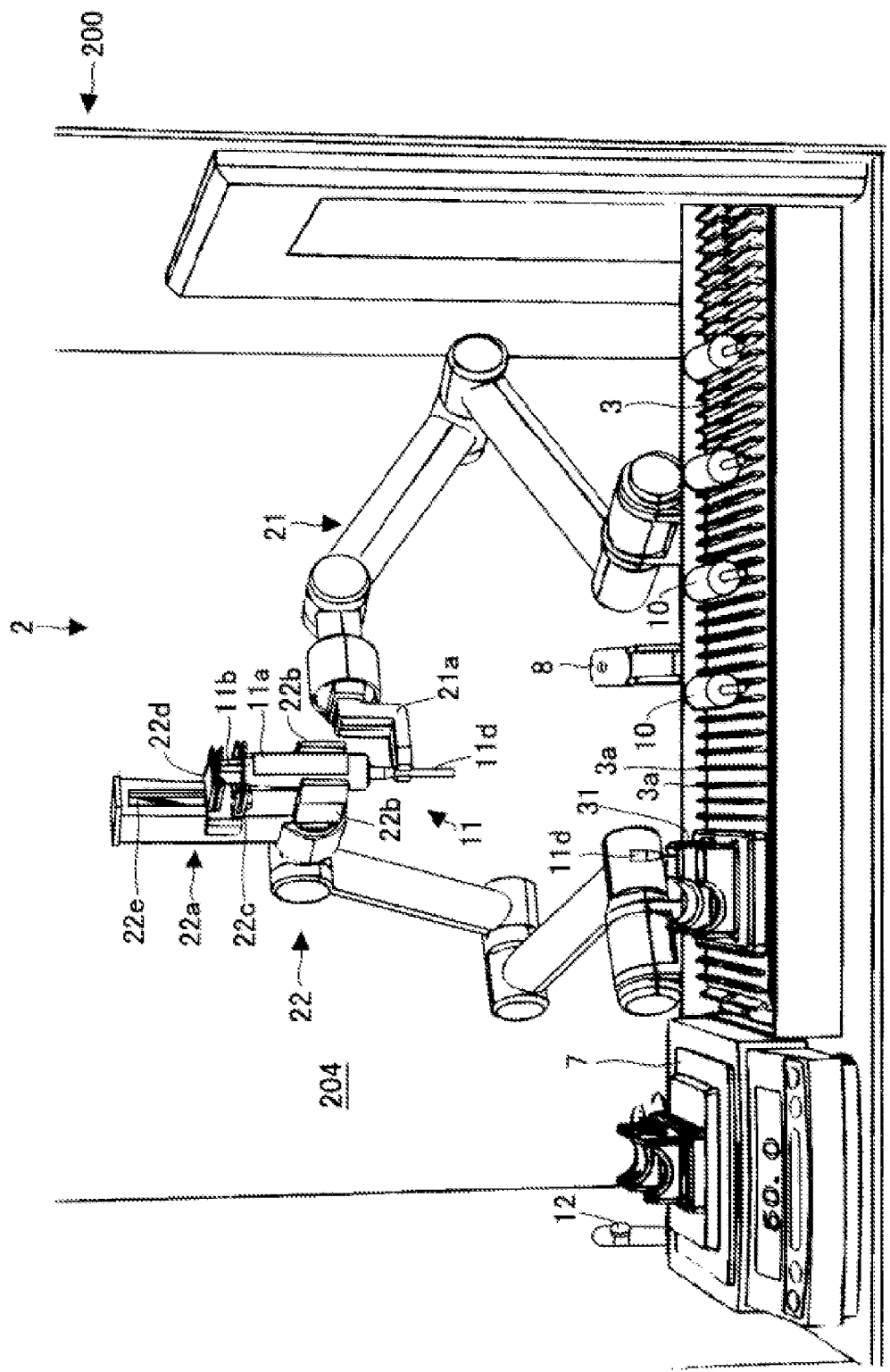
FIG. 4 is a perspective view illustrating the main body section of the coinfusion apparatus of FIG. 1.

As shown in FIG. 4, a tip of the first robot arm 21 has a grip section 21a with a pair of grip nails that opens and closes to grip an object. In this embodiment, the grip section 21a constitutes the container retention section. The pair of grip nails is screwed into feed screws (not shown) having screw sections whose threading directions are opposite to each other, for example. When this feed screw is rotated by a motor (not shown), the pair of grip nails are moved to perform a grip operation. The first robot arm 21 has a plurality of operation axes and can change the posture (inclination) of the gripped object. Then, the center side of the mutually-facing side faces (grip faces) of the pair of grip nails includes a concave section having a size suitable to grip the medical agent container 10 (in the drawing, an ampule is shown as a medical agent container). The tip end side of the grip face has a concave section having a size suitable to grip the syringe needle 11d (with a cap) of the syringe 11. In this embodiment, the syringe needle 11d is also attached/ removed by the operation of the first robot arm 21.

The tip of the second robot arm 22 has syringe retention section 22a that retains the syringe 11 and that changes the insertion amount of the piston section 11b to the cylinder section 11a of the syringe 11. For example, the syringe retention section 22a consists of a retention section for retaining the cylinder section 11a of the syringe 11 and a moving section that retains the rear part of the piston section 11b of the syringe 11 and that moves the piston section 11b. The retention section has a pair of movable nail sections 22b that sandwich the cylinder section 11a in the lateral direction and a lock section 22c for locking the flange section of the cylinder section 11a. The existence of the lock section 22c provides an advantage in that, even when the cylinder section 11a is gripped by the movable nail sections 22b with a weak force in order to prevent a change in the cross-sectional shape of the cylinder section 11a, the cylinder section 11a is prevented from moving in the axial direction (the direction in which the piston section 11b moves). The pair of movable nail sections 22b is screwed, for example, to a feed screw (not shown) having screw sections whose threading directions are opposite from each other. When the feed screw is rotated by a motor (not shown), the movable nail section 22b performs an operation to grip or to stop gripping the cylinder section 11a. Then, the moving section consists of a slider section 22d to which the rear end section of the piston section 11b is locked, a feed screw 22e to which a nut section (not shown) of this slider section 22d is screwed, and a motor (not shown) for rotating this feed screw 22e. When the feed screw 22e is rotated by the motor, the slider section 22d is moved in the direction in which the piston section 11b moves. The slider section 22d is guided, for example, by the outer face of the main body section of the syringe retention section 22a.

The second robot arm 22 includes a plurality of operation axes and can change the posture (inclination) of an object that is held. In this embodiment, the second robot arm 22 performs an operation to insert the syringe needle 11d of the syringe 11 to the mouth section of the medical agent container 10 retained by the grip section 21a (container retention section) of the first robot arm 21 and an insertion operation to insert the syringe needle 11d of the syringe 11 to the coinfusion mouth of the transfusion bag 12.

The crimped belt conveyor section 3 has crimped sections 3a at narrower intervals than the diameter of the torso section of the medical agent container 10. Two crimped sections 3a adjacent to each other have the medical agent container 10 therebetween retained so that the medical agent container 10 is floating over the belt face. The center section of each crimped section 3a has a notch section, and this notch section helps the grip section 21a of the first robot arm 21 to grip the medical agent container 10. The crimped belt conveyor section 3 can also have a syringe placement stand 31 thereon. This syringe placement stand 31 can have the syringe 11 thereon such that the syringe 11 is laid down. The center section of the syringe placement stand 31 also has a concave section. The existence of this concave section facilitates the operation by the movable nail section 22b of the second robot arm 22 to grip the cylinder section 11a. Moreover, the syringe needle 11d can be set in a standing manner in a hole formed in the syringe placement stand 31, thus facilitating the operation by the grip section 21a of the first robot arm 21 to grip the syringe needle 11d. The preparation container 103 stores therein the syringe 11 placed on the syringe placement stand 31. Thus, the syringe 11 on the syringe placement stand 31 can be entirely moved from the preparation container 103 to the belt conveyor section 3.

Figure 5:
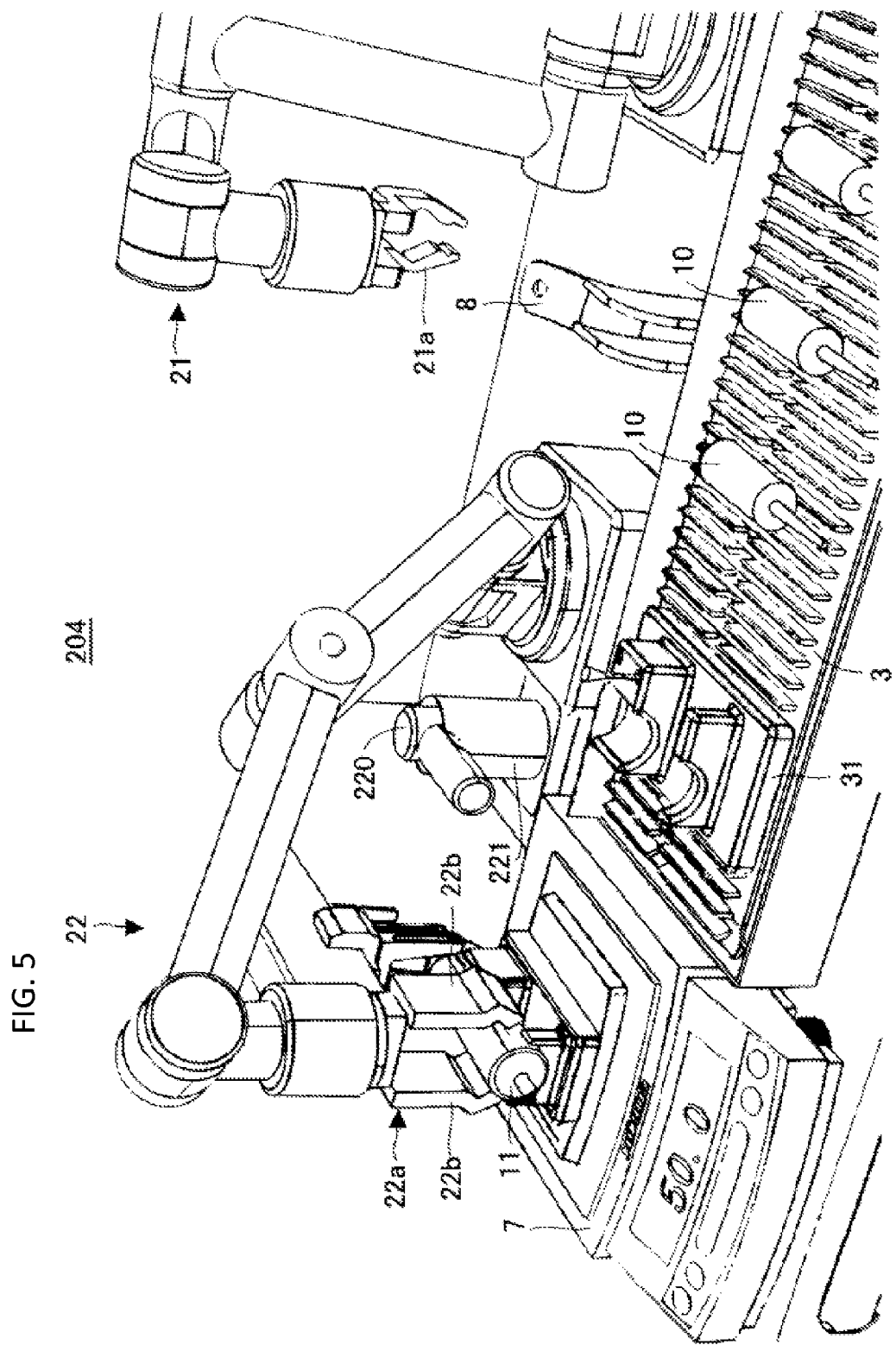
FIG. 5 is a perspective view illustrating the main body section of the coinfusion apparatus of FIG. 1.

As shown in FIG. 5, the weighing machine 7 is provided adjacent to the folded end of the crimped belt conveyor section 3. The measured value of the weighing machine 7 is displayed on a display section and is outputted to the controller. The second robot arm 22 performs an operation of using the movable nail sections 22b to grip the syringe 11 and to place this syringe 11 on the weighing machine 7. The controller causes this measurement operation to be performed, for example, when the weight of the empty syringe 11 is measured and when medicinal solution is sucked from the required number of the medical agent containers 10 into the syringe 11. By such a configuration, the controller can determine, based on a difference between the values measured by the weighing machine 7 obtained at the respective points of time, whether the syringe 11 includes therein the required amount of the medicinal solution or not. It may be configured such that the controller stops the coinfusion operation and displays an error on the display 105 if the controller determines that the syringe 11 does not contain the required amount of the medicinal solution.

Figure 6:
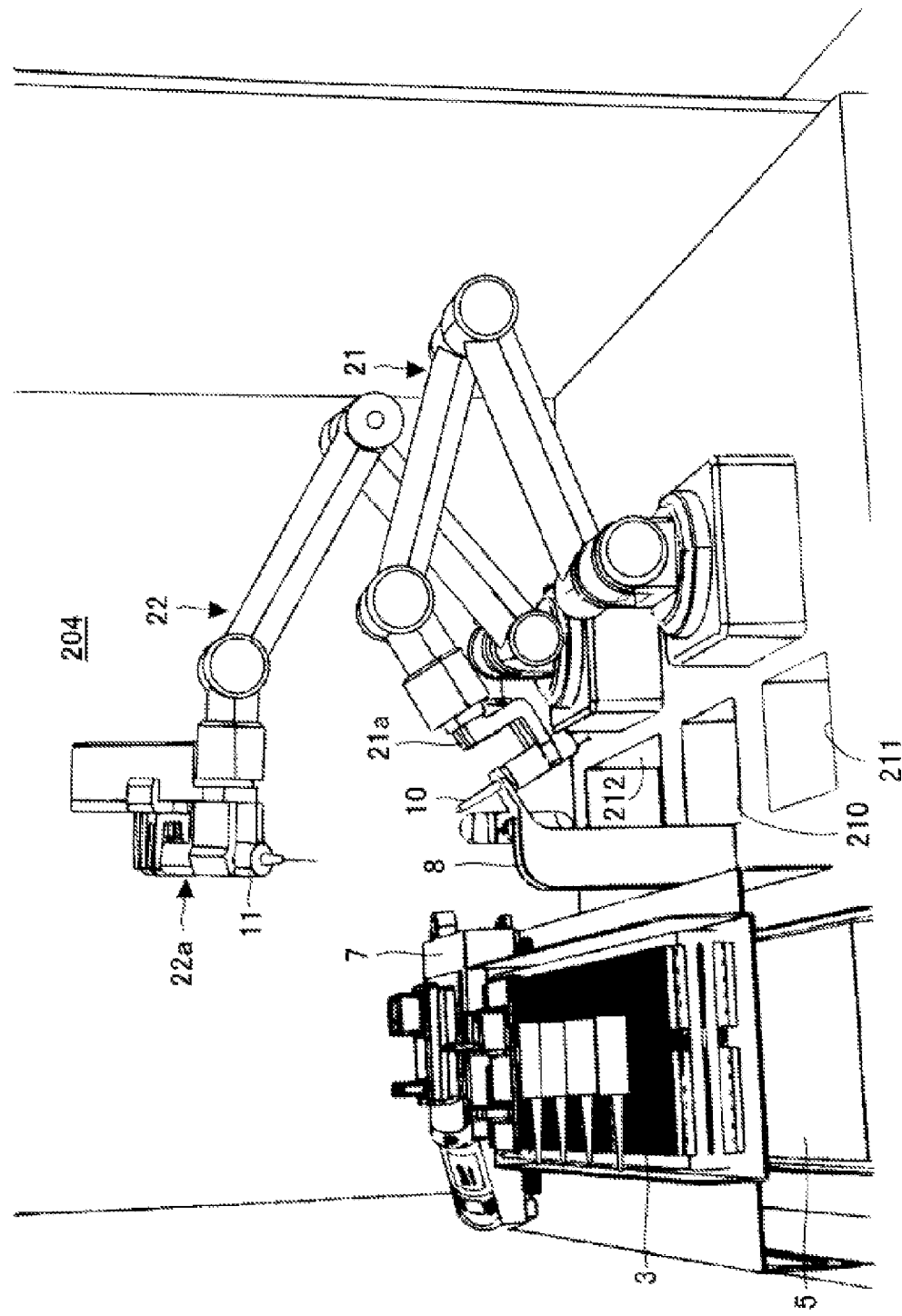
FIG. 6 is a perspective view illustrating the main body section of the coinfusion apparatus of FIG. 1.

As shown in FIG. 6, an ampule cutter 8 is provided in the front side of the first robot arm 21. This ampule cutter 8 includes a hole blade section consisting of a circular hole in which the tip of an ampule as the medical agent container 10 is inserted. The first robot arm 21 can use the grip section 21a to grip and lift the medical agent container 10 from the crimped belt conveyor section 3 and insert the tip of the medical agent container 10 to the hole blade section from the lower side.

Figure 7:
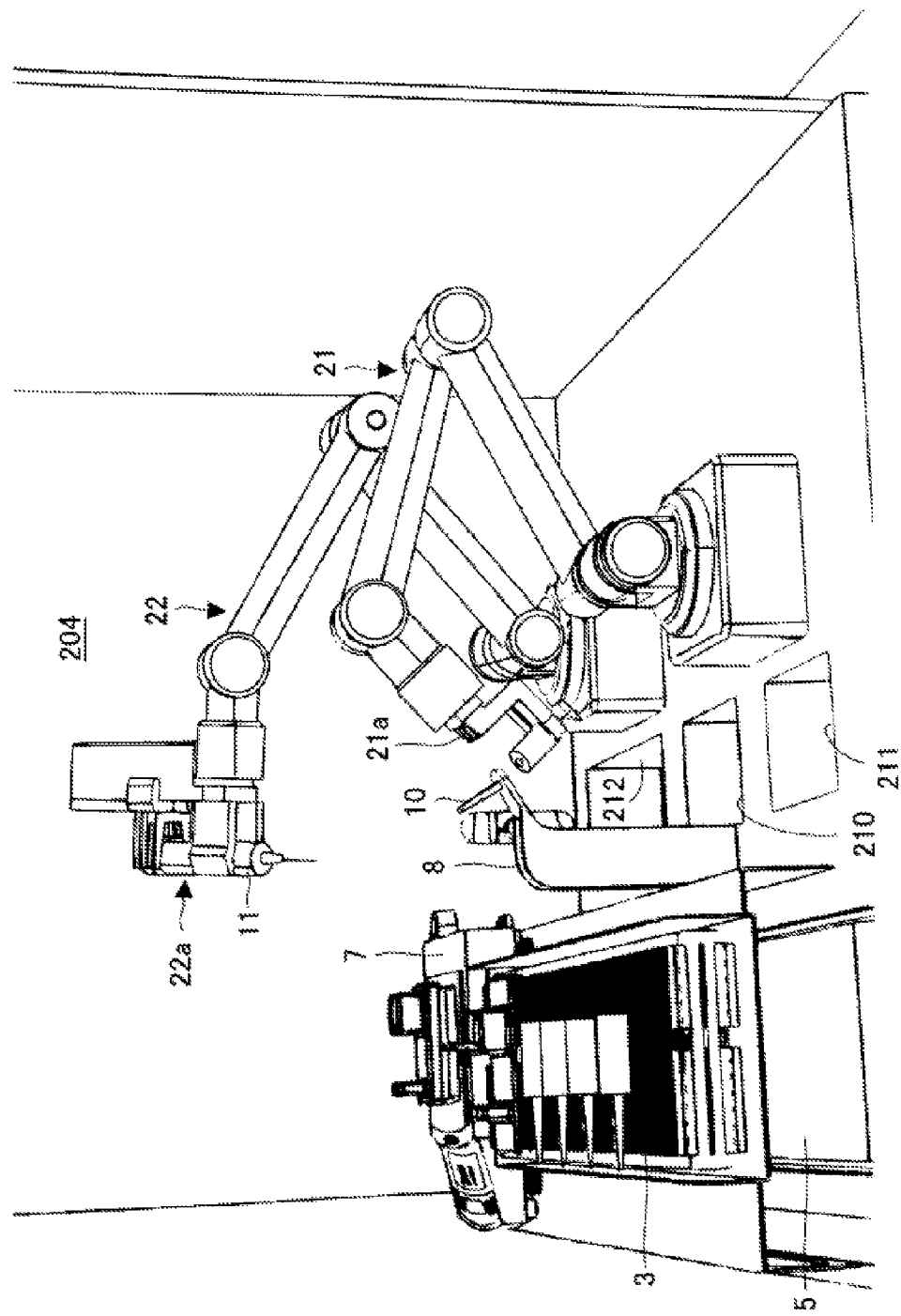
FIG. 7 is a perspective view illustrating the main body section of the coinfusion apparatus of FIG. 1.

As shown in FIG. 7, the first robot arm 21 performs the operation to incline the torso section of the medical agent container 10 while the tip of the medical agent container 10 being inserted to the hole blade section. By this operation, the tip section of the medical agent container 10 is cut off from the torso section, and the mouth section of the medical agent container 10 is exposed. Then, the tip section is dropped from the hole blade section due to a gravitational force. A dust mouth 210 is provided in the lower side of the hole blade section of the ampule cutter. Further, the dust mouth 210 is sandwiched between the dust mouths 211 and 212. These dust mouths 210, 211, and 212 are connected with the dust section 6. The dust section 6 can include therein a dust bag (not shown), and the medical agent container 10, the syringe 11, or the syringe placement stand 31 can be collected separately.

The first robot arm 21 erects the medical agent container 10 gripped by the grip section 21a such that the exposed mouth section is directed to the upper side. The second robot arm 22 erects the syringe 11 gripped by the movable nail section 22b such that the syringe needle 11d is directed to the lower side. Then, while this status is being maintained, the medical agent container 10 and the syringe 11 are moved to close to each other and the syringe needle 11d of the syringe 11 is inserted to the mouth section of the medical agent container 10. If the medical agent container 10 is a vial container having a rubber cap, the syringe needle 11d is straightly inserted to the rubber cap.

Figure 8:
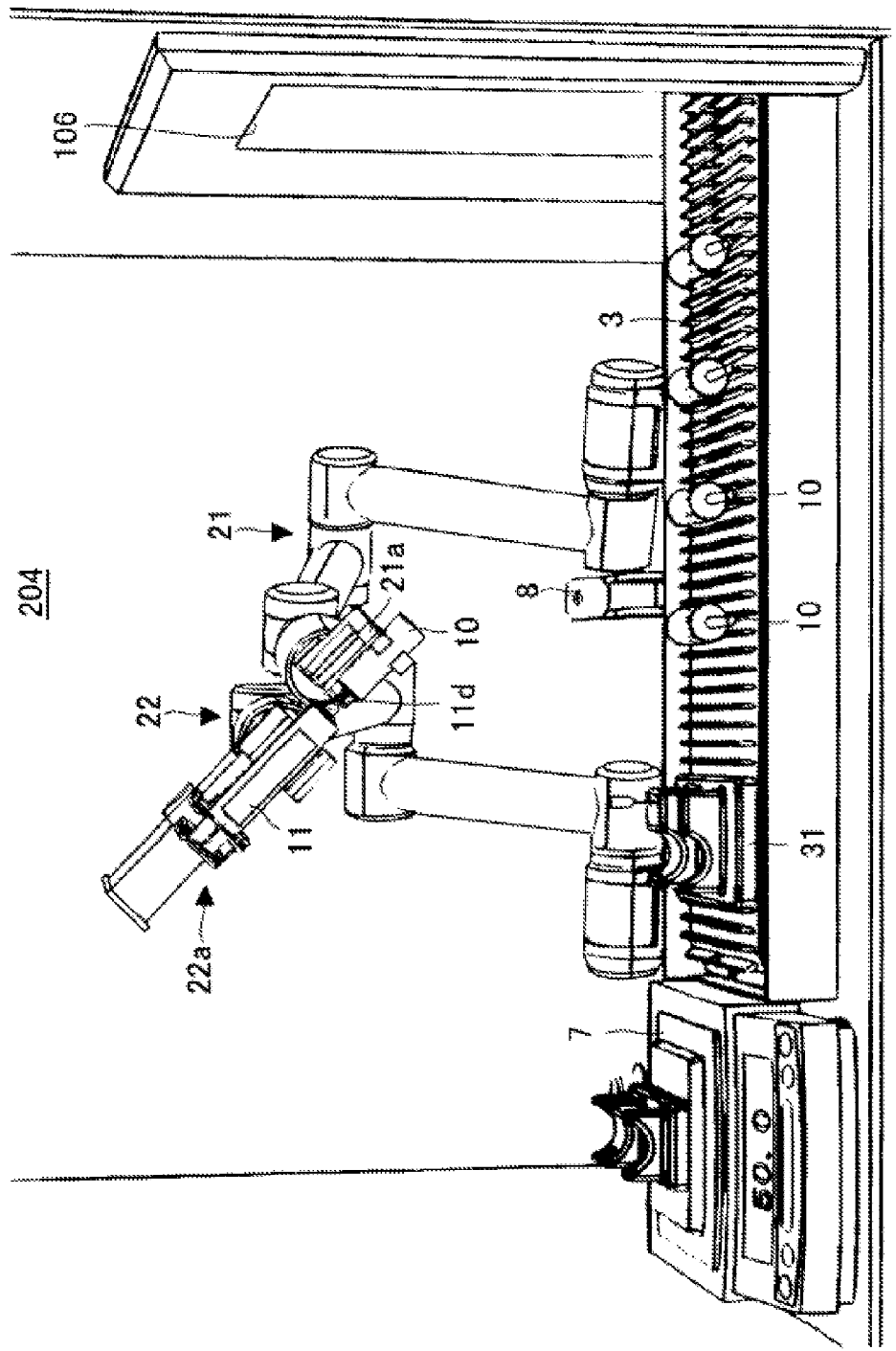
FIG. 8 is a perspective view illustrating the main body section of the coinfusion apparatus of FIG. 1.

As shown in FIG. 8, the first robot arm 21 and the second robot arm 22 incline the postures of the medical agent container 10 and the syringe 11 when the medicinal solution in the medical agent container 10 is sucked into the syringe 11. When the medical agent container 10 is an ampule, a certain amount of liquid drug is sucked from the medical agent container 10, and then, the medical agent container 10 is inclined by approximately 100 degrees from the vertical direction so that the medicinal solution is moved to the mouth section side (neck section). Thus, the maximum amount of the medicinal solution can be sucked without causing the tip of the syringe needle 11d of the syringe 11 to have a contact with the bottom of the medical agent container 10.

Figure 9:
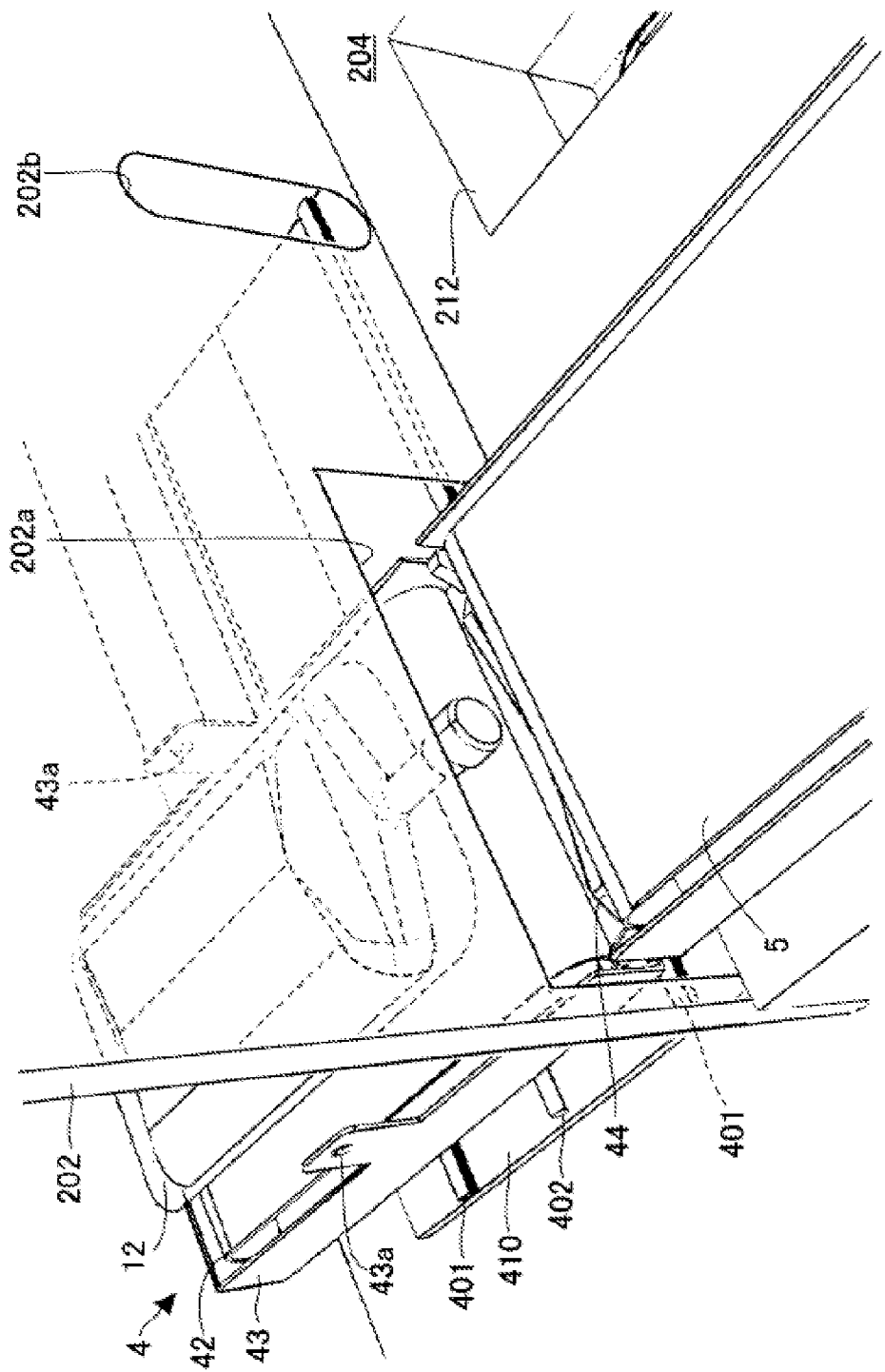
FIG. 9 is a perspective view illustrating the transfusion bag retention section of the main body section of the coinfusion apparatus of FIG. 1.

As shown in FIG. 9, the division plate 202 has a transfusion bag pass mouth 202a in the vicinity of the folded end of the transfusion bag conveying section 5. The transfusion bag retention section 4 is provided at the outer side of the division plate 202 so as to be opposed to the folded end of the transfusion bag conveying section 5. The transfusion bag retention section 4 consists of a main body section 41 (see FIG. 12 as the main body section 41 is not shown in FIG. 9), a conveyor section 42, a conveyor support section 43, and a chuck section 44. The controller can operate the transfusion bag conveying section 5 to transfer the transfusion bag 12 to the transfusion bag retention section 4. Further, the controller operates the conveyor section 42 to thereby move the transfusion bag 12 onto the conveyor support section 43.

The chuck section 44 consists of a pair of nail sections. For example, a gear section (not shown) formed at the base end-side of each nail section is meshed with a worm gear. The base end side and the tip end side of each nail section have a rotation supporting point therebetween. The rotation of the worm gear causes each nail section to rotate to thereby perform the chuck operation. When the transfusion bag 12 is moved onto the conveyor section 42, the chuck section 44 is open so as not to hinder this move. The worm gear or the like of the chuck section 44 is provided at the lower side of the conveyor support section 43. Thus, the worm gear moves to a different position in accordance with a change of the position of the conveyor support section 43 so that the coinfusion mouth of the transfusion bag 12 is retained. Of course, the chuck section 44 having a mechanism different from the above can also be used.

Figure 10:
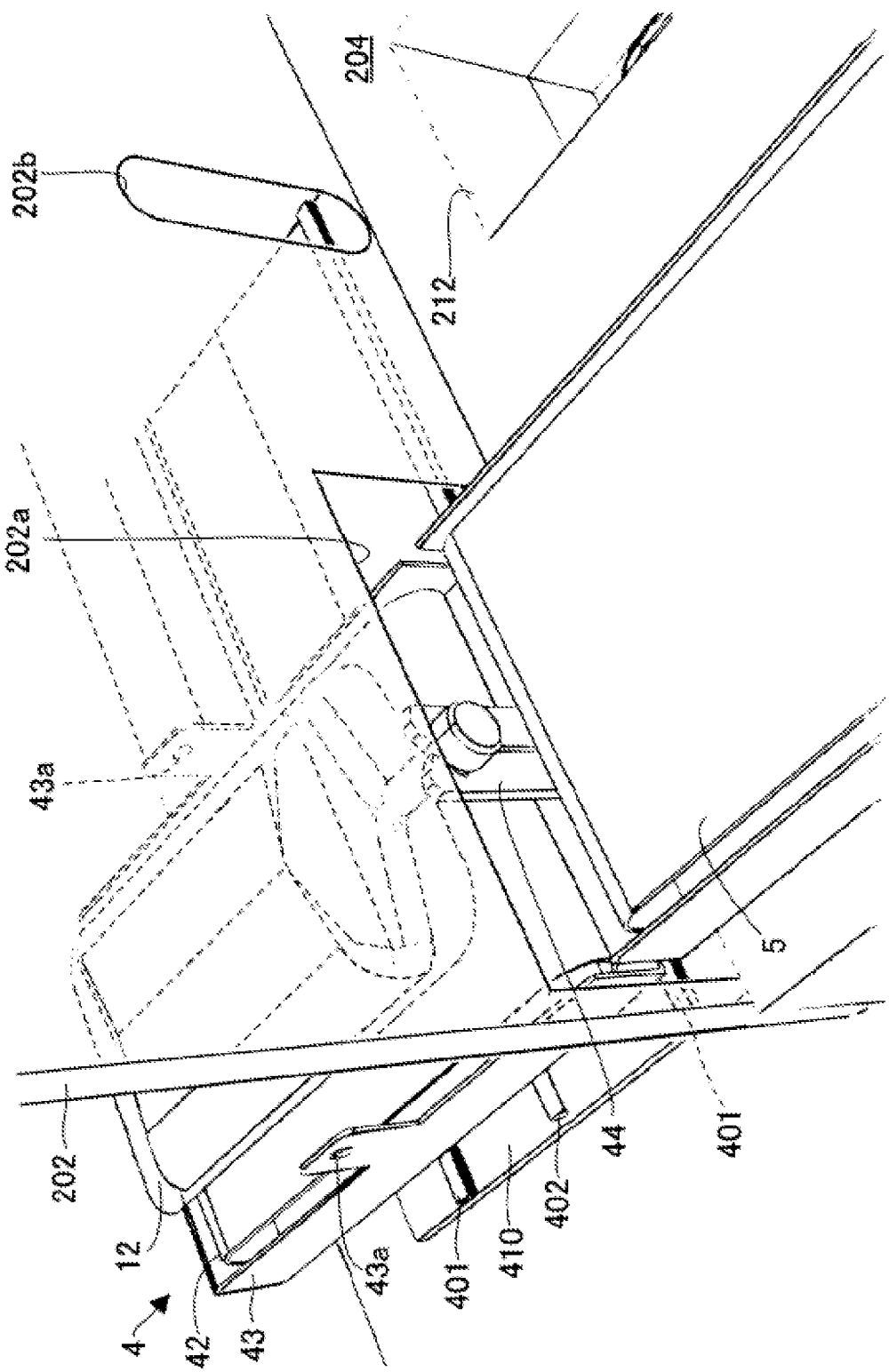
FIG. 10 is a perspective view illustrating the transfusion bag retention section of the main body section of the coinfusion apparatus of FIG. 1.

When the transfusion bag 12 is entirely moved onto the conveyor section 42, the chuck section 44 sandwiches the coinfusion mouth of the transfusion bag 12 in the lateral direction as shown in FIG. 10. In order to judge whether the transfusion bag 12 is entirely and completely moved onto the conveyor section 42, a video camera may also be provided at the upper side of the transfusion bag retention section 4 to subject an image taken by this video camera to an image analysis to thereby determine if the transfusion bag 12 has reached a predetermined position. Alternatively, a photosensor or the like for sensing the coinfusion mouth of the transfusion bag 12 may be provided at the transfusion bag pass mouth 202*a* so as to determine that the transfusion bag 12 has reached a predetermined position when the sensor senses the coinfusion mouth of the transfusion bag 12. Of course, other methods can also be used to determine if the transfusion bag 12 is entirely and completely moved onto the conveyor section 42.

A guide groove is provided at the lower face of the main body section 41 of the transfusion bag retention section 4. This guide groove is engaged with a guide concave section 401 of the support table 410 for supporting the transfusion bag retention section 4. The guide concave section 401 is formed in a direction orthogonal to the direction in which the transfusion bag 12 is conveyed by the conveyor section 42 (a direction along the division plate 202). A moving nut (not shown) is provided at the lower side of the main body section 41, and this moving nut is screwed with the feed screw 402. This feed screw 402 is provided on the support table 410. When this feed screw 402 is rotated by a motor (not shown), the transfusion bag retention section 4 is guided by the guide concave section 401 and is moved to further inside.

Figure 11:
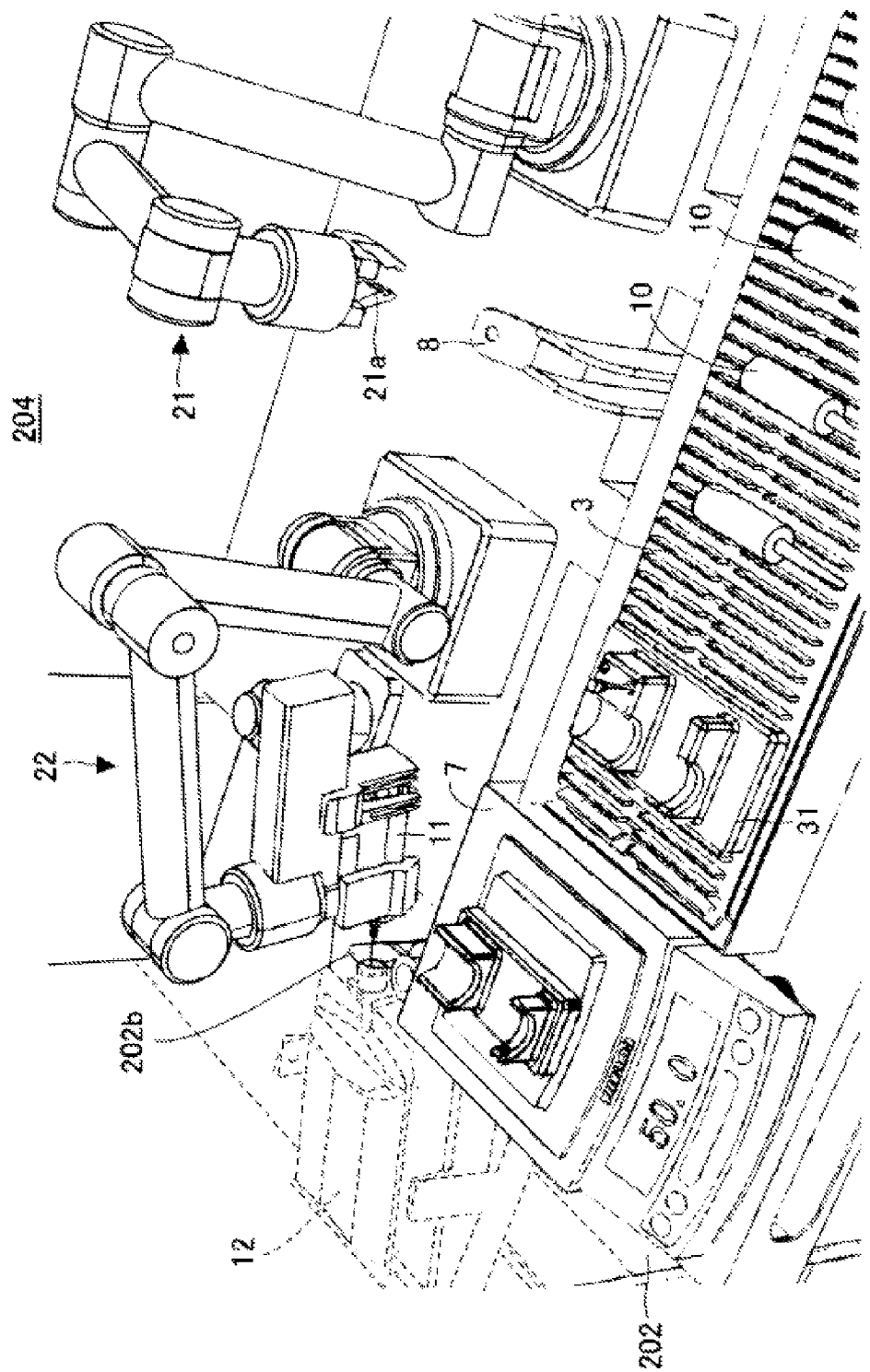
FIG. 11 is a perspective view illustrating the main body section of the coinfusion apparatus of FIG. 1.
Figure 12:
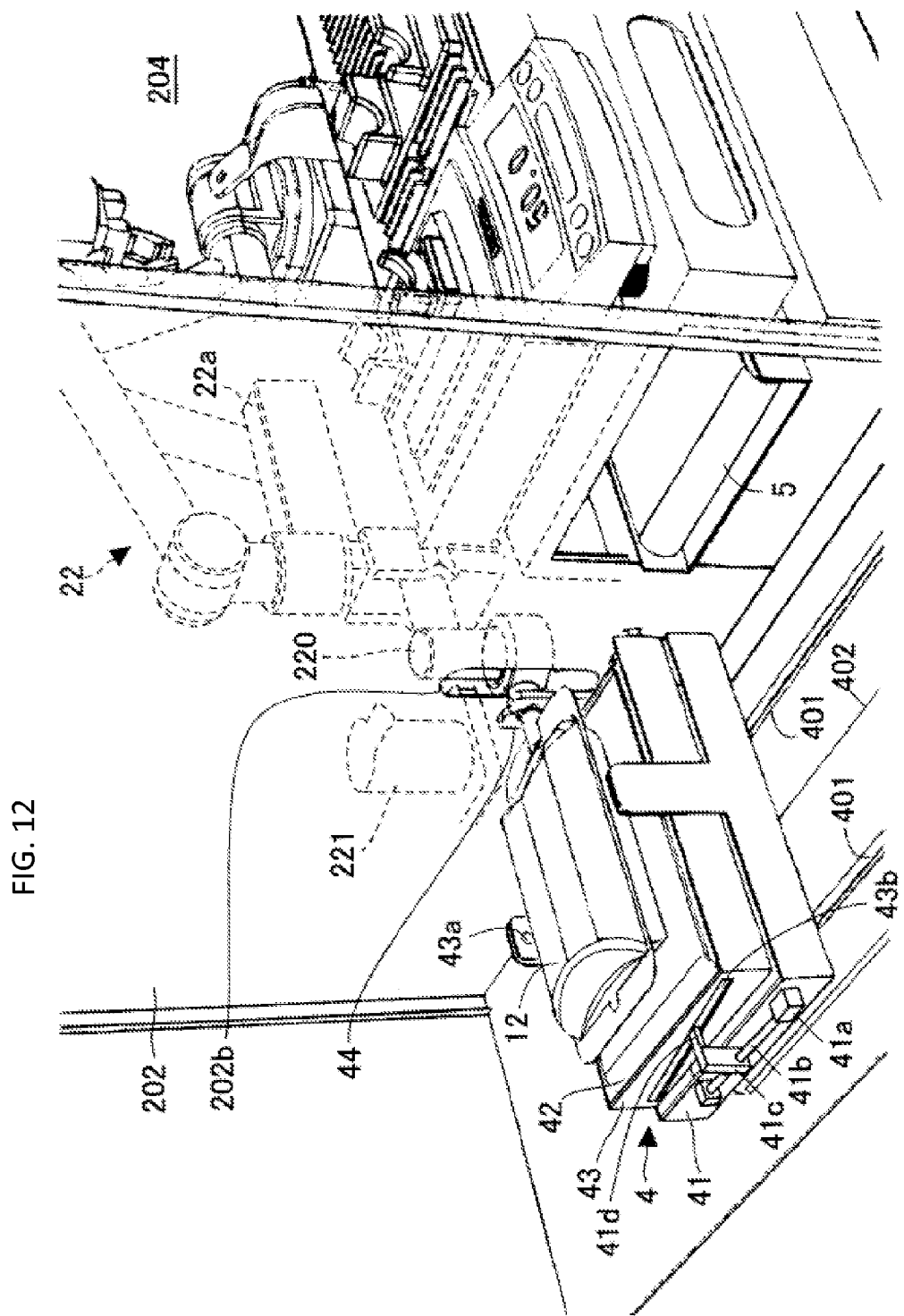
FIG. 12 is a perspective view illustrating the transfusion bag retention section of the main body section of the coinfusion apparatus of FIG. 1.

As shown in FIG. 11 and FIG. 12, the division plate 202 has a coinfusion communication mouth 202*b* that is formed at a position at which the coinfusion mouth of the transfusion bag 12 is positioned when the transfusion bag retention section 4 is moved to the deepest side. This coinfusion communication mouth 202*b* has an oblong shape. The coinfusion communication mouth 202*b* may be designed to open or close by a shutter or the like. Then, the conveyor support section 43 supporting the conveyor section 42 in the transfusion bag retention section 4 is rotatably supported by the main body section 41 by screwing the support hole 43*a* with a protrusion section (not shown) of the main body section 41. The rotation of the conveyor support section 43 causes the transfusion bag 12 to oscillate in a seesaw-like manner to thereby direct the coinfusion mouth in the downward or upward direction.

For example, the rear end face of the main body section 41 has the feed screw 41*b* rotated by the motor 41*a* that is screwed with the moving nut 41*c*, and the rotation of the motor 41*a* causes the moving nut 41*c* to move in the lateral direction. The rear end face of the conveyor support section 43 has an engagement groove 43*b* formed in the oblique lateral direction. This engagement groove 43*b* is engaged with the protrusion section 41*d* of the moving nut 41*c*. As a result, the rotation of the motor 41*a* causes the protrusion section 41*d* to raise or lower the rear end of the conveyor support section 43, thus allowing the conveyor support section 43 to perform the oscillation operation. Of course, a mechanism different from the above-described one can be used to cause the conveyor support section 43 to oscillate.

The second robot arm 22 inserts the syringe needle 11*d* of the syringe 11 from the coinfusion communication mouth 202*b* to the coinfusion mouth of the transfusion bag 12 with its coinfusion mouth facing in the downward or upward direction on the conveyor section 42, for example. Then, the syringe retention section 22*a* is operated to inject the medicinal solution in the syringe 11 into the transfusion bag 12. After this injection, the weight of the syringe 11 may be measured by the weighing machine 7. The controller can determine, based on this weight measurement, whether the medicinal solution corresponding to the required amount in the syringe 11 was injected to the transfusion bag 12 or not. After the weight measurement, the controller causes the second robot arm 22 or the like to perform an operation to dispose the syringe 11 or the like.

The coinfusion processing room 204 has a cleaning tool 220 and a holding section 221 for housing the cleaning tool 220. The controller causes, after disposal of the syringe 11 or the like, the second robot arm 22 to perform an operation to grip the handle of the cleaning tool 220. The controller also causes the cleaning tool 220 to perform an operation of cleaning the coinfusion mouth of the transfusion bag 12.

After the cleaning, the controller stops the operation of the chuck section 44 of locking the coinfusion mouth and allows the conveyor section 42 to move. As a result, the transfusion bag 12 already subjected to the coinfusion and cleaning is guided from the rear end side thereof toward the bagging apparatus 300.

As shown in FIG. 1, the bagging apparatus 300 receives the transfusion bag 12 dropped from the rear end side through the mouth section 301 and performs a bagging operation. The bagging apparatus 300 may be an existing bagging mechanism such as a linear reciprocating type packaging machine or a rotary-type packaging machine. The bagging apparatus 300 includes: the supply section 302 for sending out transparent vinyl used for making a bag; the packing section 303 for packing the transfusion bag 12, which is received through the mouth section 301, with the transparent vinyl; the oscillation section 304 for oscillating the packing section 303; and the storage section 306 having a storage container 305 for receiving the transfusion bag 12 inclined and dropped by this oscillation section 304, for example.

When the storage container 305 has a size that is large enough to hold one transfusion bag 12, it means that a space to hold the medical agent container 10, the syringe 11 and the like can be eliminated, thus allowing the storage container 305 to have a size smaller than that of the preparation container 103. In other words, the transfusion bag 12 taken out of the preparation container 103 is subjected to a coinfusion processing and the transfusion bag 12 already subjected to the coinfusion is moved into another storage container 305 having a size smaller than that of the preparation container 103, thus the size to the storage section 306 can be small in the coinfusion apparatus 1.

As shown in FIG. 1, the coinfusion processing room 204 has a monitoring camera 205. The controller may allow an image taken by the monitoring camera 205 to be recorded in a recording section (not shown) (e.g., hard disk drive).

As described above, because the coinfusion apparatus 1 includes the coinfusion operation section 2, the coinfusion apparatus 1 can automatically perform a part or the entirety of the coinfusion processing. Also, the transfusion bag 12 is positioned at the outer side of the coinfusion processing room 204, and therefore, the transfusion bag 12 can be prevented from being subjected to the radiation exposure due to medicinal solution. Moreover, because the cleaning tool 220 is used to clean the coinfusion mouth of the transfusion bag 12, the coinfusion mouth can be prevented from being left with medicinal solution attached thereto. Furthermore, the existence of the bagging apparatus 300 allows the clean transfusion bag 12 that was not exposed to radiation to be transferred to a processing room.

Figure 13:
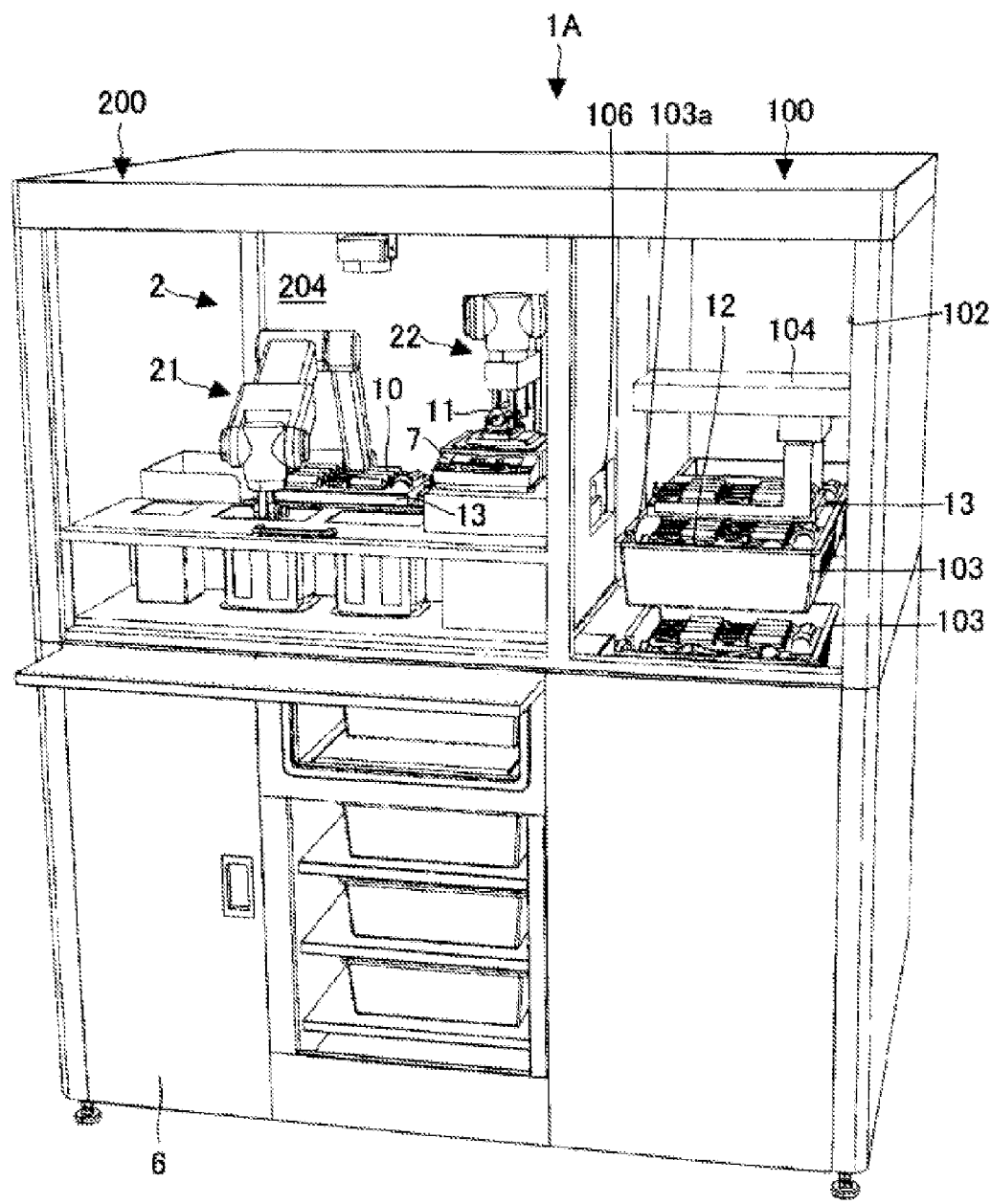
FIG. 13 is a perspective view illustrating a coinfusion apparatus according to another embodiment of this invention.

The coinfusion apparatus 1A shown in FIG. 13 is a coinfusion apparatus that does not include the bagging apparatus 300, the transfusion bag retention section 4, the crimped belt conveyor section 3, and the transfusion bag conveying section 5 and the like. The preparation container 103 in this coinfusion apparatus 1A has an adjustment case 13. This adjustment case 13 includes the required number of medical agent containers 10 and syringes 11. The supply robot 104 provided in the supply room 100 of the coinfusion apparatus 1A removes the adjustment case 13 from the preparation container 103 and transfers this adjustment case 13 from the communication mouth 106 into the coinfusion processing room 204 of the main body section 200. This transfer operation allows the adjustment case 13 to be guided to a determined position and allows the first robot arm 21 and the second robot arm 22 to accurately grip the medical agent container 10 and the syringe 11. In this coinfusion apparatus 1A, the position of the first robot arm 21 and the position of the second robot arm 22 are mutually exchanged, and the second robot arm 22 is provided at a position close to the communication mouth 106. The weighing machine 7 is provided in front of the second robot arm 22. The lower side of the stand on which the weighing machine 7 is placed has a space through which the adjustment case 13 passes.

Figure 14:
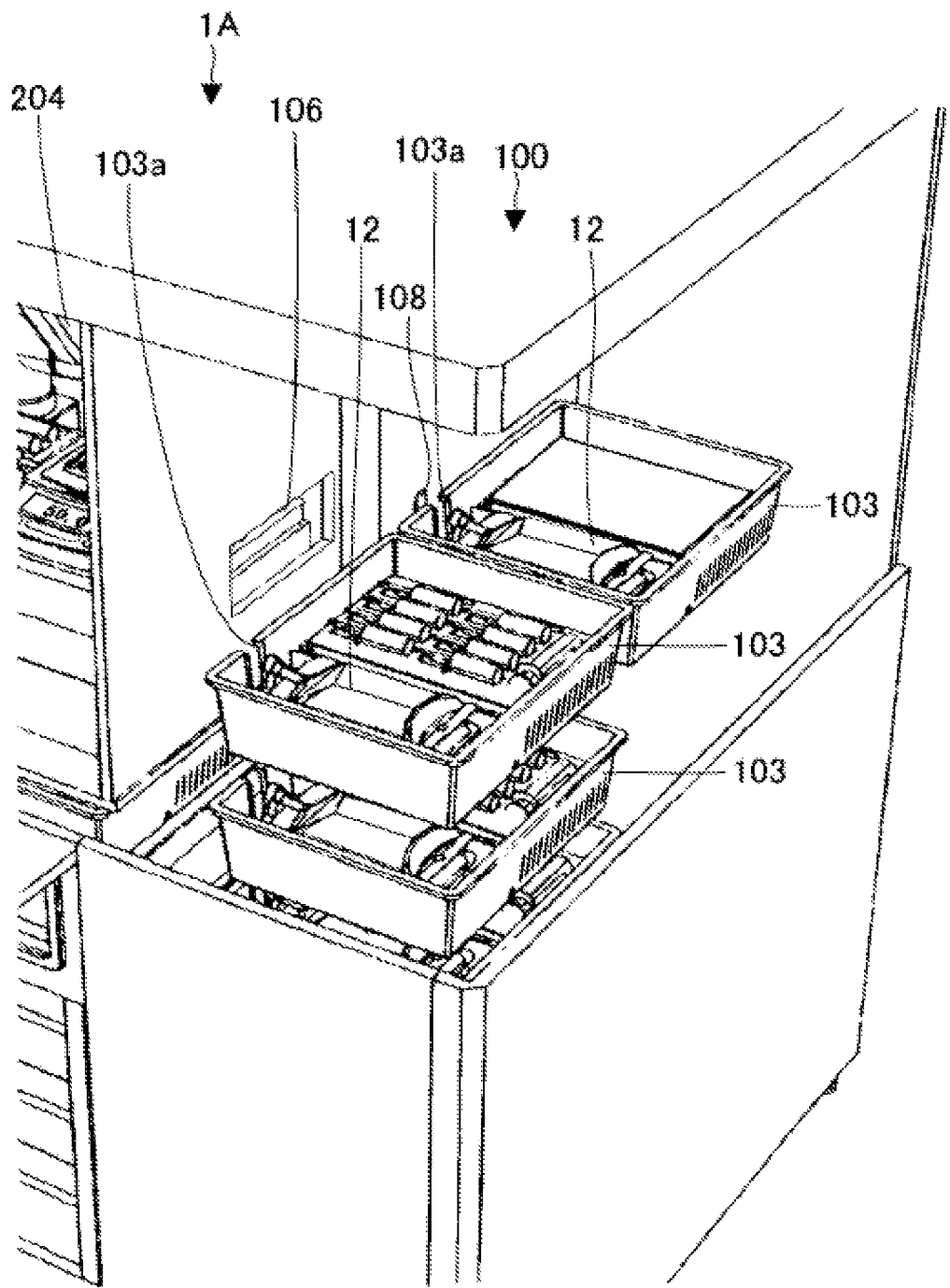
FIG. 14 is an enlarged perspective view illustrating the supply section of the coinfusion apparatus of FIG. 13.

The preparation container 103 in this coinfusion apparatus 1A includes therein the transfusion bag 12 that is laid down such that the coinfusion mouth thereof faces the communication mouth 106. That is, in this coinfusion apparatus 1A, the preparation container 103 includes therein the transfusion bag oscillation stand 113a for retaining the transfusion bag 12. A side face of the preparation container 103 opposed to the coinfusion mouth of the transfusion bag 12 has a cut region 103a as shown in FIG. 14. Thus, the syringe needle can be inserted to the coinfusion mouth without the need to remove the transfusion bag 12 from the preparation container 103.

In the shown example, the syringe 11 or the medical agent container 10 is removed from the preparation container 103 through the communication mouth 106 to the coinfusion processing room 204. Thereafter, the preparation container 103 is moved to the deeper inside (by the transfer by the conveyor or by the pushing operation by the supply robot 104 for example). Then, the coinfusion mouth of the transfusion bag 12 in the preparation container 103 is placed at a position at which the coinfusion communication mouth 108 is formed. The coinfusion communication mouth 108 can be used to insert the syringe needle of the syringe 11 to the coinfusion mouth of the transfusion bag 12 from the coinfusion processing room 204. It is also possible to have a configuration in which the communication mouth 106 also functions as the coinfusion communication mouth 108.

Figure 15A:
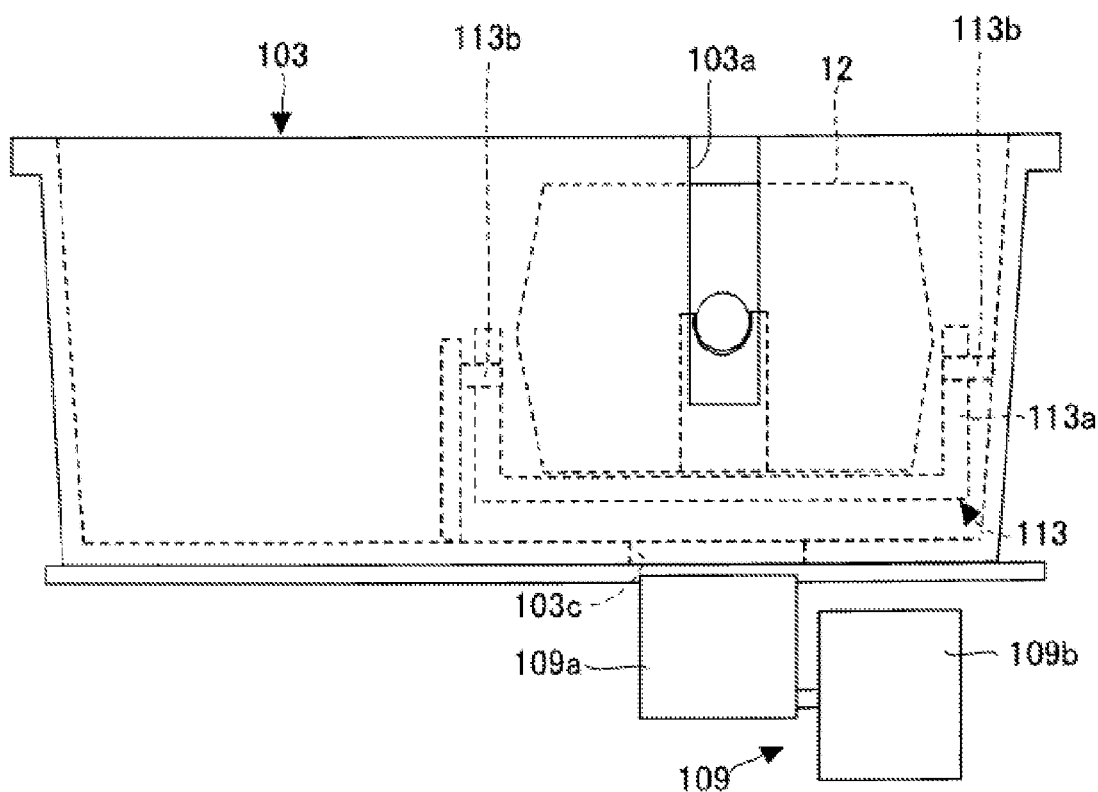
FIG. 15A is a front view illustrating a transfusion bag oscillation mechanism provided in the preparation container of FIG. 13.
Figure 15B:
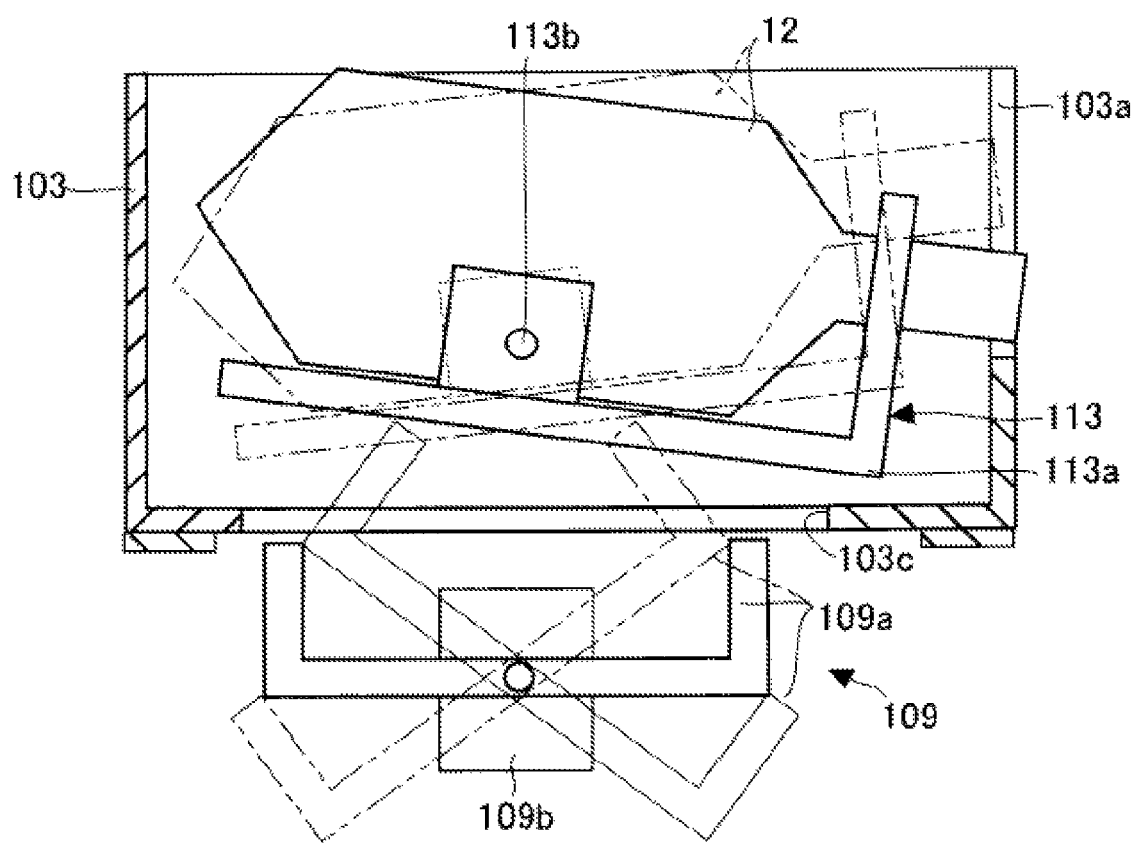
FIG. 15B is a side view illustrating the transfusion bag oscillation mechanism provided in the preparation container of FIG. 13.

As shown in FIG. 15A and FIG. 15B, the preparation container 103 may include therein the oscillation mechanism 113 for oscillating the transfusion bag 12 so that when the syringe needle of the syringe 11 is inserted to the coinfusion mouth of the transfusion bag 12, the coinfusion mouth may be inclined in the oblique upward direction or in the oblique downward direction. Specifically, the oscillation mechanism 113 is configured such that the transfusion bag oscillation stand 113a provided in the preparation container 103 can be oscillated by the horizontal axis 113b in a seesaw-like manner. The transfusion bag oscillation stand 113a has a chuck section (not shown) for fixing the coinfusion mouth of the transfusion bag 12. The preparation container 103 has a mouth 103c at the bottom section thereof. Through this mouth 103c, the operation piece 109a of the seesaw operation section 109 provided at the coinfusion apparatus 1-side can be abutted to the lower face of the transfusion bag oscillation stand 113a to thereby oscillate this transfusion bag oscillation stand 113a. The operation piece 109a is operated by the motor 109b to rotate. The motor 109b is controlled by the controller. When the preparation container 103 is moved to the deeper inside, the operation piece 109a is positioned in the horizontal direction so as to avoid hindering this move.

After the required amount of medicinal solution is sucked from the medical agent container 10 into the syringe 11, the second robot arm 22 causes the syringe needle of the syringe 11 to be directed from the coinfusion communication mouth 108 to the interior of the supply control room 102 and the syringe needle is inserted from the cut region 103a to the coinfusion mouth of the transfusion bag 12. Then, the second robot arm 22 injects the medicinal solution in the syringe 11 into the transfusion bag 12. The syringe 11 whose medical solution has already been injected, the medical agent container 10, and the adjustment case 13 are disposed from the dust mouth to the dust section 6. In this case, the preparation container 103 includes therein the transfusion bag 12 already subjected to the coinfusion process. The preparation container 103 including the transfusion bag 12 is entirely removed from the supply control room 102.

The above-mentioned coinfusion apparatus 1A is also configured such that the transfusion bag 12 is placed outside the coinfusion processing room 204, and this can prevent the transfusion bag 12 from being exposed to radiation due to medical agent. Furthermore, this coinfusion apparatus 1A does not require the transfusion bag 12 to be moved significantly, which allows the apparatus to have a smaller size. This coinfusion apparatus 1A may also be configured to have a crimped belt conveyor section to transfer the medical agent container 10 or the like. Another configuration may also be used in which the supply control room 102 is adjacent to the bagging apparatus so that the transfusion bag 12 already subjected to the coinfusion process is lifted by the supply robot 104 and is given to the bagging apparatus. This bagged transfusion bag 12 may be returned to the original preparation container 103 or may also be held in another small storage container sufficient to accommodate one transfusion bag.

Figure 16:
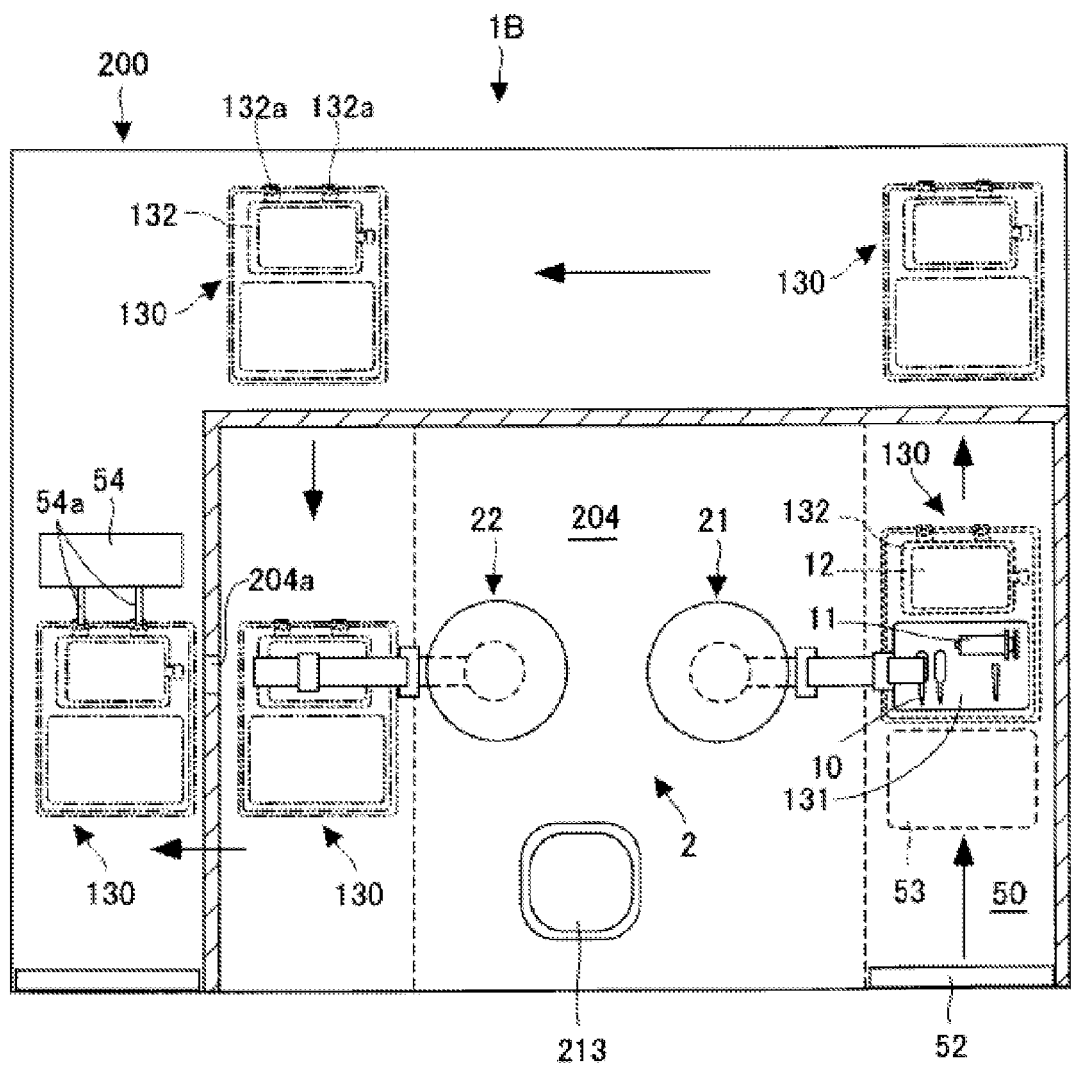
FIG. 16 is an explanatory view illustrating the coinfusion apparatus according to another embodiment of this invention.
Figure 17:
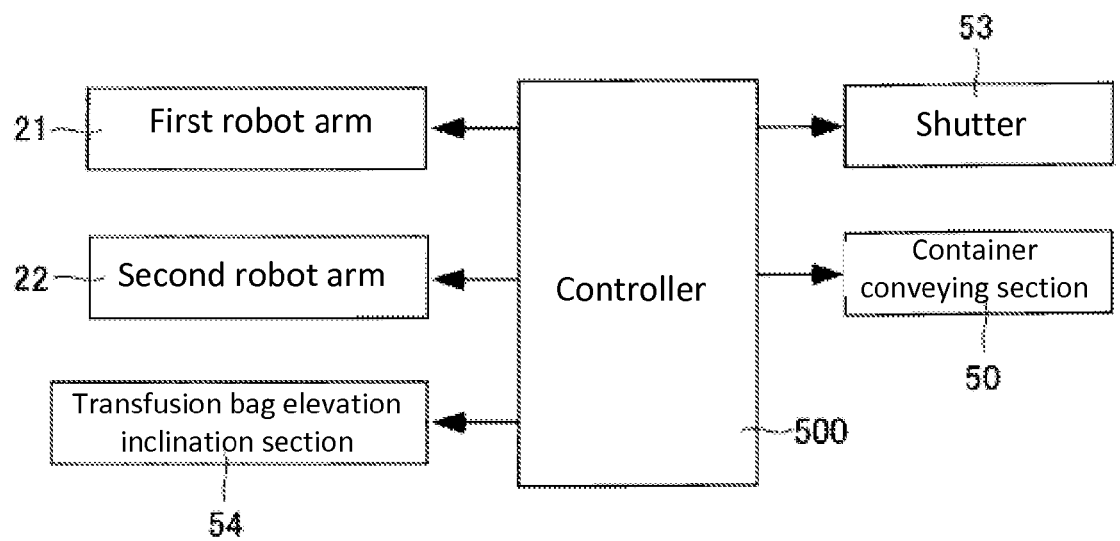
FIG. 17 is a schematic block view illustrating the control system of the coinfusion apparatus of FIG. 16.

The coinfusion apparatus 1B shown in FIG. 16 is a coinfusion apparatus that is configured, as in the coinfusion apparatus 1A, not to include the bagging apparatus 300, the transfusion bag retention section 4, the crimped belt conveyor section 3, and the transfusion bag conveying section 5 and the like. FIG. 17 illustrates a schematic configuration of the control system of this coinfusion apparatus 1B. As in the coinfusion apparatus of other embodiments, the first robot arm 21, the second robot arm 22 and the like of the coinfusion apparatus 1B are controlled by the controller 500.

The preparation container 130 in the coinfusion apparatus 1B includes therein the medical agent tray 131 on which the medical agent container 10 and the syringe 11 are placed and the transfusion bag retention section 132 for retaining the transfusion bag 12. The former and the latter are separately and movably provided, respectively. The transfusion bag retention section 132 has a chuck section (not shown) for fixing the coinfusion mouth of the transfusion bag 12. When the medical agent container 10 is an ampule, then this ampule is set so as to obliquely stand, instead of being laid down on the medical agent tray 131. When the ampule is set in this manner, it is possible to prevent the medical agent from being collected in the neck section of the ampule.

As is the case with the coinfusion apparatus of other embodiments, the coinfusion operation section 2 of the coinfusion apparatus 1B includes the first robot arm 21 functioning as a container retention section and the second robot arm 22 functioning as a syringe retention section at the left and right sides, and they perform the operation to insert the syringe needle of the syringe 11 to the mouth section of the medical agent container 10 retained by the second robot arm 22 and also perform the operation to insert the syringe needle of the syringe 11 to the coinfusion mouth of the transfusion bag 12.

The coinfusion apparatus 1B has the base end sections of the first robot arm 21 and the second robot arm 22 provided at the ceiling side. This makes it easy to clean the floor of the coinfusion processing room 204. The coinfusion apparatus 1B also has the container conveying section 50 for transferring the preparation container 130 from the position close to the first robot arm 21 to the position close to the second robot arm 22. When the preparation container 130 is transferred to a position close to the first robot arm 21, the first robot arm 21 supplies the medical agent container 10 and the syringe 11 into the coinfusion processing room 204. When the preparation container 130 is transferred to the position close to the second robot arm 22, an operation is performed to position the coinfusion mouth of the transfusion bag 12 retained by the transfusion bag retention section 132 of the preparation container 130 at the coinfusion communication mouth 204a formed in the coinfusion processing room 204.

The lower surface of the coinfusion processing room 204 has a mouth under which the dust box 213 communicating with the coinfusion processing room 204 is placed. The container conveying section 50 is provided so as to transfer the preparation container 130 at the lower side of the coinfusion processing room 204 and at the rear side of the dust box 213. This configuration allows the dust box 213 to be taken in or taken out at the front face side of the coinfusion apparatus. In order to show the transfer path of the container conveying section 50, FIG. 16 shows the preparation container 130 transferred in the container conveying section 50 by the two-dot chain line. It does not mean that the container conveying section 50 includes a plurality of adjustment containers 130 at the same time.

The left side of front face of the coinfusion apparatus 1B has a cover 52 communicating with the container conveying section 50. This cover 52 can be opened to place the preparation container 130 into the container conveying section 50. When the controller 500 determines that the preparation container 130 has reached a specified position in the container conveying section 50 based on the driving pulse number of a transfer motor (not shown) or an output from a position detection sensor, the controller temporarily stops the transfer of the preparation container 130. At this stop position, the shutter 53 providing the communication between the container conveying section 50 and the coinfusion processing room 204 is slidably provided in the horizontal direction.

The container conveying section 50 has an elevating section to raise and lower the medical agent tray 131 in the preparation container 130 stopped at the stop position. This elevating section raises the medical agent tray 131 from the lower side by four shafts provided so as to be raised and lowered, for example. The lower face of the preparation container 130 includes penetration holes through which the four shafts pass.

After stopping the preparation container 130, the controller 500 elevates the medical agent tray 131 and opens the shutter 53. When the shutter 53 is opened, the medical agent tray 131 is exposed to the coinfusion processing room 204. In FIG. 16, the medical agent tray 131, the syringe 11 and the like are exposed to the interior of the coinfusion processing room 204.

Then, the controller 500 controls the first robot arm 21 and the second robot arm 22, and causes the first robot arm 21 to grip the syringe 11 on the medical agent tray 131 exposed to the coinfusion processing room 204 and this syringe 11 is received by the second robot arm 22. The medical agent container 10 of the medical agent tray 131 is temporarily stored in a holder (not shown) of the coinfusion processing room 204 by the first robot arm 21. In the coinfusion apparatus 1B, the first robot arm 21, the elevating section, and the shutter 53 constitute a supply section that supplies the medical agent container 10 and the syringe 11 into the coinfusion processing room 204.

After placing all of the medical agent container 10 and the like from the medical agent tray 131 into the coinfusion processing room 204, the controller 500 performs an operation to lower the shaft of the elevating section, an operation to close the shutter 53, and an operation to transfer the preparation container 130 to a position close to the second robot arm 22. In the above-described coinfusion apparatus 1A, the supply robot 104 removes the adjustment case 13 in which the medical agent container 10 and the syringe 11 are set from the preparation container 103 and places the adjustment case 13 in the coinfusion processing room 204 of the main body section 200. On the other hand, the coinfusion apparatus 1B has a configuration that enables the first robot arm 21 to grip the medical agent container 10 or the like on the medical agent tray 131 and to place it into the coinfusion processing room 204. Thus, the medical agent tray 131 remains in the preparation container 130 and the medical agent tray 131 can be used repeatedly.

A position that is in the container conveying section 50 and that is close to the second robot arm 22 has a transfusion bag elevation inclination section 54. The transfusion bag retention section 132 in the preparation container 130 has two engagement hole sections 132a that are provided to protrude from the edge of the preparation container 130. The controller 500 transfers the preparation container 130 to the front side of the transfusion bag elevation inclination section 54 and subsequently allows the hook section 54a of the transfusion bag elevation inclination section 54 to be engaged with the engagement hole section 132a from the lower side to raise the transfusion bag retention section 132, thus allowing the coinfusion mouth of the transfusion bag 12 to be positioned at the coinfusion communication mouth 204a. The transfusion bag elevation inclination section 54 can incline the transfusion bag retention section 132 to face the coinfusion mouth of the transfusion bag 12 in an upward or downward direction. When syringe needle is pulled out from the coinfusion mouth of the transfusion bag 12, the controller 500 controls the transfusion bag elevation inclination section 54 to direct the coinfusion mouth in the upward direction. By directing the coinfusion mouth in the upward direction as described above, the syringe needle can be pulled out without a risk of liquid leakage from the coinfusion mouth of the transfusion bag 12.

The upper side of the coinfusion apparatus 1B has a fan apparatus (not shown). Outside air is supplied through a filter to the interior of the coinfusion processing room 204 and the interior of the container conveying section 50. By making the amount of air sucked and emitted higher than that of supplied air, the coinfusion processing room 204 and the container conveying section 50 are allowed to have therein a negative pressure. By sucking and emitting a higher amount of air from the coinfusion processing room 204 than from the container conveying section 50, the container conveying section 50 has therein a positive pressure as compared with the pressure in the coinfusion processing room 204. Therefore, even when the coinfusion processing room 204 communicates with the container conveying section 50 while the shutter 53 is open, the air in the coinfusion processing room 204 is prevented from flowing to the container conveying section 50.

In the coinfusion apparatus 1B, one preparation container 130 is manually supplied to the container conveying section 50. However, another configuration may be used where many adjustment containers 103 stacked to one another are sequentially supplied to the container conveying section 50 in an automatic manner. Another configuration may be used in which the ceiling of the coinfusion processing room 204 has an ultraviolet germicidal lamp to sterilize the interior of the coinfusion processing room 204 before and after the coinfusion processing. Alternatively, the ultraviolet germicidal lamp may be provided between the first robot arm 21 and the second robot arm 22 in order to thoroughly irradiate the interior of the coinfusion processing room 204 with ultraviolet rays. Alternatively, instead of supplying the preparation container 130 from the front face side of the coinfusion apparatus 1B into the container conveying section 50, the preparation container 130 may be supplied from the side face of the coinfusion apparatus 1B into the container conveying section 50. The preparation container 130 may also be discharged from either the front face or the side face of the coinfusion apparatus 1B.

In these embodiments, the coinfusion operation section 2 was configured by a robot arm. However, an operation to retain and rotate the syringe 11, for example, may also be performed by the rotation mechanism disclosed in Patent Document 1. Also, in these embodiments, the preparation container 103 in which the transfusion bag 12, the medical agent container 10, and the syringe 11 are set is supplied to the supply section 100, but the invention is not limited to such a preparation container 103. For example, in the supply control room 102 of the supply section 100, a position at which the medical agent container is placed, a position at which the syringe is placed, and a position at which the transfusion bag is placed may also be predetermined in advance, for example. Thus, the operator can set the required medical agent container 10, the syringe 11, the transfusion bag 12 and the like at the respective positions.

When the medical agent container 10 is a vial container in which powder-like medical agent is contained, a processing is performed to insert the syringe needle of the syringe 11 to the transfusion bag 12 to suck the transfusion from the transfusion bag 12 into the syringe 11 and to pour this sucked transfusion into the vial container. The sucking operation is desirably performed such that the transfusion bag 12 is inclined to direct the coinfusion mouth in an obliquely-downward direction. When the transfusion is poured into the vial container, the syringe 11 and the vial container are desirably inclined as shown in FIG. 8 to prevent the transfusion from directly poured (or foamed) onto the medical agent at the bottom of the vial container. Alternatively, after the transfusion is poured into the vial container, the first robot arm 21 for gripping the vial container may be used to shake this vial container so that the medical agent can be securely dissolved into the transfusion. It is preferable that this shaking operation is composed of one or both of a linear reciprocating movement to the vial container and a rotation movement for rotating the vial container. Alternatively, instead of allowing the first robot arm 21 to perform the shaking operation as described above, the coinfusion processing room 204 may include an exclusive shaking apparatus such that the vial container is passed from the first robot arm 21 to the exclusive shaking apparatus.

As described above, the embodiments of this invention have been described with reference to the drawings. However, this invention is not limited to the shown embodiments. Various changes or modifications can be made to the shown embodiment within the scope that is the same or equivalent to that of this invention.

The invention claimed is:

1. A coinfusion apparatus for moving medicinal solution in a medical agent container into a transfusion bag, comprising:
    a first robot arm for retaining the medical agent container;
    a second robot arm for retaining a syringe and for changing an insertion amount of a piston part to a cylinder part in the syringe; and
    a preparation container that includes a removable adjustment case for supplying the medical agent container and the syringe,
    wherein the second robot arm performs an operation to insert a syringe needle of the syringe to a mouth section of the medical agent container and an operation to insert the syringe needle of the syringe to a coinfusion mouth of a transfusion bag.

2. The coinfusion apparatus according to claim 1, wherein the removable adjustment case is transferred to a position close to the first and second robot arms through a communication opening by a supply robot arm which is provided in a supply room.

3. The coinfusion apparatus according to claim 2, wherein a side face of the preparation container which is opposed to the coinfusion mouth of the transfusion bag has a cut region such that the syringe needle of the syringe is inserted through the communication opening to the coinfusion mouth of the transfusion bag without removing the transfusion bag from the preparation container.

4. The coinfusion apparatus according to claim 1, wherein a side face of the preparation container which is opposed to the coinfusion mouth of the transfusion bag has a cut region such that the syringe needle of the syringe is inserted through a coinfusion communication opening to the coinfusion mouth of the transfusion bag without removing the transfusion bag from the preparation container.

5. The coinfusion apparatus according to claim 1, wherein the preparation container further includes an oscillation mechanism which is configured to oscillate the transfusion bag so that when the syringe needle of the syringe is inserted to the coinfusion mouth of the transfusion bag, said coinfusion mouth is inclined in an oblique upward direction or in an oblique downward direction.

6. The coinfusion apparatus according to claim 5, wherein the oscillation mechanism is configured to oscillate the transfusion bag in a see-saw manner using horizontal axes.

7. The coinfusion apparatus according to claim 1, further comprising a dust box provided at a lower side of the coinfusion apparatus,
   wherein after performing the operation of inserting the syringe needle of the syringe to the mouth section of the medical agent container and the operation of inserting the syringe needle of the syringe to the coinfusion mouth of the transfusion bag, the medical agent container and the syringe are disposed from a dust opening to the dust box.

8. A coinfusion apparatus for moving medicinal solution in a medical agent container into a transfusion bag, comprising:
   a first robot arm for retaining the medical agent container;
   a second robot arm for retaining a syringe and for changing an insertion amount of a piston part to a cylinder part in the syringe, wherein the second robot arm performs an operation to insert a syringe needle of the syringe to a mouth section of the medical agent container and an operation to insert the syringe needle of the syringe to a coinfusion mouth of a transfusion bag;
   a coinfusion processing room accommodating the first robot arm and the second robot arm; and
   a container conveying section for transferring a preparation container at an outer side of the coinfusion processing room,
   wherein a base end of the first robot arm and a base end of the second robot arm are provided at a ceiling of the coinfusion processing room.

9. The coinfusion apparatus according to claim 8, wherein the preparation container further comprises a movable tray for supplying the medical agent container and the syringe and a movable transfusion bag retention tray for retaining the transfusion bag.

10. The coinfusion apparatus according to claim 9, wherein when the preparation container is transferred to a position close to the first robot arm, an elevating section of the container conveying section raises the movable tray and a shutter providing communication between the container conveying section and the coinfusion processing room opens, allowing the first robot arm to transfer the medical agent container and the syringe from the movable tray into the coinfusion processing room.

11. The coinfusion apparatus according to claim 10, wherein after transferring the medical agent container and the syringe into the coinfusion processing room, the elevation section of the container conveying section lowers the movable tray, the shutter closes, and the container conveying section transfers the preparation container to a position close to the second robot arm.

12. The coinfusion apparatus according to claim 9, further comprising a transfusion bag elevation inclination section having engaging hooks that can be attached to engagement hole sections protruding from an edge of the preparation container.

13. The coinfusion apparatus according to claim 12, wherein when the preparation container is transferred to a position close to the second robot arm, the transfusion bag elevation inclination section raises the movable transfusion bag retention tray allowing for positioning of the coinfusion mouth of the transfusion bag in front of a communication opening in an upward direction or in a downward direction.

14. The coinfusion apparatus according to claim 8, wherein the syringe needle is pulled out from the coinfusion mouth of the transfusion bag while the coinfusion mouth being directed in an upward direction.

15. The coinfusion apparatus according to claim 8, wherein the container conveying section has a higher pressure than the coinfusion processing room.

16. The coinfusion apparatus according to claim 8, wherein a dust box is provided at a lower surface of the coinfusion processing room so as to dispose the medical agent container and the syringe through a dust opening.

17. The coinfusion apparatus according to claim 16, wherein the container conveying section is configured to transfer the preparation container at a lower side of the coinfusion processing room and at a rear side of the dust box.

* * * * *